US007556964B2

(12) United States Patent
Ishii et al.

(10) Patent No.: US 7,556,964 B2
(45) Date of Patent: Jul. 7, 2009

(54) TRANSGENIC CELL AND GENE RECOMBINANT ANIMAL HAVING A MUTANT SDHC GENE DERIVED FROM MAMMALS

(76) Inventors: Naoaki Ishii, 3-3-6 Takamoridai, Isehara, Kanagawa 259-1115 (JP); Takamasa Ishii, 2-9 Fujimi-cho, Yokosuka, Kanagawa 238-0021 (JP)

( * ) Notice: Subject to any disclaimer, the term of this patent is extended or adjusted under 35 U.S.C. 154(b) by 167 days.

(21) Appl. No.: 10/867,168

(22) Filed: Jun. 15, 2004

(65) Prior Publication Data

US 2005/0278797 A1 Dec. 15, 2005

(51) Int. Cl.

| | |
|---|---|
| ***C12N 5/00*** | (2006.01) |
| ***C12N 15/00*** | (2006.01) |
| ***C12N 15/63*** | (2006.01) |
| ***A01N 43/04*** | (2006.01) |
| ***C12N 15/11*** | (2006.01) |
| *G01N 33/00* | (2006.01) |
| *A01K 67/00* | (2006.01) |

(52) U.S. Cl. .................... 435/325; 435/320.1; 435/440; 435/455; 514/44; 536/23.1; 800/3; 800/8; 800/21

(58) Field of Classification Search ....................... None
See application file for complete search history.

(56) References Cited

OTHER PUBLICATIONS

Bockamp et al., 2001, Physiol. Genomics 11:115-132.*

Bishop, 1996, Reproductive Nutrition and Development 36: 607-616.*

Rulicke and Hubischer, 2000, Experimental Physiology 85: 589-601.*

Holschneider et al., 2001, Int J. Devl. Neuroscience 18:615-618.*

Fischer et al., 1996. FASEB Journal vol. 10, pp. 126-136.*

Guo et al (2003, J. Biol. Chem. 278:47629-47635.*

Yankovskaya et al (2003, Science 299:700-704.*

Yanase et al (2002, Mechanism of Aging and Development 123:1579-1587.*

Cadenas et al., "Mitochondrial free radical generation, oxidative stress and aging," Free Radical Biology & Medicine, vol. 29, No. 3/4, pp. 222-230, (2000).

Lenaz, "The Mitochondrial Production of Reactive Oxygen Species: Mechanisms and Implications in Human pathology," IUBMB Life, vol. 52, pp. 159-1614, (2001).

Chen et al., "Production of Reactive Oxygen Species by Mitochondria," Journal of Biological Chemistry, vol. 278, No. 38, pp. 36027-36031, (2003).

Turrens, "Superoxide Production by the Mitochondrial Respiratory Chain," Bioscience Reports, vol. 17, No. 1, pp. 3-8, (1997).

Liu, "Cooperation of a "Reactive Oxygen Cycle" with the Q Cycle and The Proton Cycle in the Respiratory Chain—Superoxide Generating and Cycling Mechanisms in Mitochondria," Journal of Bioenergetics and Biomembranes, vol. 31, No. 4, pp. 367-376, (1999).

(Continued)

*Primary Examiner*—Robert M. Kelly
*Assistant Examiner*—Kelgainamane Hiriyanna
(74) *Attorney, Agent, or Firm*—Greenblum & Bernstein, P.L.C.

(57) ABSTRACT

It is an object of the present invention to provide a transgenic cell and gene recombinant animal having a mutant SDHC gene, which enables the examination of the action of reactive oxygen species (ROS) derived from mitochondria in mammals. The present invention provides a transgenic animal cell and a gene recombinant non-human mammal, which are characterized in that a mutant SDHC gene derived from mammals is introduced, and that reactive oxygen species (ROS) are excessively produced.

6 Claims, 18 Drawing Sheets

OTHER PUBLICATIONS

Jacobson, "Reactive oxygen species and programmed cell death," TIBS, vol. 21, pp. 83-86, (1996).
Mignotte et al., "Mitochondria and apoptosis," European Journal of Biochemistry, vol. 252, pp. 1-15, (1998).
On page 1 of the specification of the present application; Floyd, "Role of oxygen free radicals in carcinogenesis and brain ischemia," FASEB Journal, vol. 4, pp. 2587-2597, (1990).
Cerutti et al., "Inflammation and Oxidative Stress in carcinogenesis," Cancer Cells, vol. 2, pp. 1-7, (1991).
Kovacic et al., "Mechanisms of Carcinogenesis: Focus on Oxidative Stress and Electron Transfer," Current Medicinal Chemistry, vol. 8, pp. 773-796, (2001).
Hassan et al., "Paraqual and *Escherichia coli*," The Journal of Biological Chemistry, vol. 254, No. 21, pp. 10846-10852, (1979).
Feng et al., "Mitochondrial Electron Transport is a Key Determinant of Life Span in *Caenorhabditis elegans*," Developmental Cell, vol. 1, pp. 633-644, (2001).
Aitken et al., "Reactive Oxygen Species Generation by Human Spermatozoa is Induced by Exogenous NADPH and Inhibited by the Flavoprotein Inhibitors Diphenylene Iodonium and Quinacrine," vol. 47, pp. 468-482, (1997).
Saybasili et al., "Effect of Mitochondrial Electron Transport Chain Inhibitors on Superoxide Radical Generation in Rat Hippocampal and Striatal Slices," Antioxidants & Redox Signaling, vol. 3, No. 6, pp. 1099-1104, (2001).
Ishii et al., "A methyl viologen-sensitive mutant of the nematode *Caenorhabditis elegans*," Mutation Reaearch, vol. 237, pp. 165-171, (1990).
Senoo-Matsuda et al., "A Defect in the Cytochrome B Large Subunit in Complex II Causes Both Superoxide Anion Overproduction and Abnormal Energy Metabolism in *Caenorhabditis elegans*," The Journal of Biological Chemistry, vol. 276, No. 45, pp. 41553-41558, (2001).
Isshi et al., "A mutation in succinate dehydrogenase cytochrome b causes oxidative stress and ageing in nematodes," Nature, vol. 394, pp. 694-697, (1998).
Senoo-Matsuda et al., "A Complex II Defect Affects Mitochondrial Structure, Leading to *ced*-3- and *ced*-4-dependent Apoptosis and Aging," The Journal of Biological Chemistry, vol. 278, No. 24, pp. 22031-22036, (2003).
Honda et al., "Oxygen-Dependent Perturbation of Life Span and Aging Rate in the Nematode," Journal of Gerontology, vol. 48, No. 2, pp. B57-B61, (1993).
Hosokawa et al., "Rapid accumulation of fluorescent material with aging in an oxygen-sensitive mutant *mev*-1 of *Caenorhabditis elegans*," Mechanisms of Aging and Development, vol. 74, pp. 161-170, (1994).
Neimann et al., "Mutations in SDHC cause autosomal dominant paraganglioma, type 3," nature genetics, vol. 26, pp. 268-270, (2000).
Collins, "Generation and initial analysis of more than 15,000 full-length human and mouse cDNA sequences," PNAS, vol. 99, No. 26, pp. 16899-16903, (2002).
Paddenberg et al., "Essential role of complex II of the respiratory chain in hypoxia-induced ROS generation in the pulmonary vasculature," American Journal of Physiology—Lung Cellular and Molecular Physiology, vol. 284, pp. L710-L719, (2003).
Yu et al., "Cytochrome $b_{560}$ (QPs1) of Mirochondiral Succinate-Ubiquinone Reductase," The Journal of Biological Chemistry, vol. 267, No. 34, pp. 24508-24515, (1992).
Stratil et al., "Linkage and radiation hybrid mapping of the procine gene for subunit C of succinate dehydrogenase complex (SDHC) to chromosome 4," Animal Genetics, vol. 32, pp. 105-121, (2001).
Neimann et al., "Autosomal dominant malignant and catecholamine-producing paraganglioma caused by a splice donor site mutation in SDHC," Hum Genet, vol. 113, pp. 92-94, (2003).
Elbehti-Green et al., "Characterization of the human *SDHC* gene encoding one of the integral membrane protein of succinate—quinone oxidoreductase in mitochondria," Gene, vol. 213, pp. 133-140, (1998).
Hirawake et al., "Cytochrome *b* in human complex II (succinate-ubiquinone oxidoreductase): cDNA cloning of the components in liver mitochondria and chromosome assignment of the genes for the large (SDHC) and small (SDHD) subunits to 1q21 and 11q23," Cytogenet Cell Genet, vol. 79, pp. 132-138, (1997).
Yang et al., "The Quinone-binding Site in Succinate-ubiquinone Reductase from *Escherichia coli*," The Journal of Biological Chemistry, col. 273, No. 48, pp. 31916-31923, (1998).
Yankovskaya et al., "Architecture of Succinate Dehydrogenase and Reactive Oxygen Species Generation," Science, vol. 299, pp. 700-704, (2003).
Zhang et al., "Ageing and apoptosis," Mechanisms of Ageing and Development, vol. 123, pp. 245-260, (2002).
Floyd et al., "Oxidative stress in brain aging Implications for therapeutics of neurodegenerative diseases," Neurobiology of Aging, vol. 23, pp. 795-807, (2002).
Simonian et al., "Oxidative stress in Neurodegenerative stress," Annu, Rev. Parnacol. Toxicol., vol. 36, pp. 83-106, (1996).
Mattson, "Apoptosis in Neurodegenerative Disorders," Nature Reviews: Molecular Cell Biology, vol. 1, pp. 120-129, (2000).
Melov, "Mitochondrial Oxidative Stress," Annals New York Academy of Sciences, vol. 908, pp. 219-225. (2000).
Samper et al., "Mitochondrial oxidative stress causes chromosomal instability of mouse embryonic fibroblasts," Aging Cell, vol. 2, pp. 277-285, (2003).
Hogan et al., "Manipulating the Mouse Embryo: A Laboratory Manual," Cold Spring Harbor Press,(1986).
Gordon et al., "Genetic transformation of mouse embryos by microinjection of purified DNA," Proceedings of National Academy of the United States of America, col. 77, No. 12, pp. 7380-7384, (1980).
Gordon and Ruddle, "Integration and Stable Germ Line Transmission of Genes Injected into Mouse Pronuclei," Science, vol. 214, 1244-1246, (1981).
Palmiter and Brinster, "Transgenic Mice," Cell, vol. 41, pp. 343-345, (1985).
Brinster et al., "Factors affecting the efficiency of introducing foreign DNA into mice by microinjecting eggs," Proceedings of National Academy of United States of America, vol. 82, pp. 4438-4442, (1985).
Ishii et al., "Coenzyme $Q_{10}$ can prolong *C. elegans* lifespan by lowering oxidative stress," Mechanisms of Ageing Development, Vo. 125, pp. 41-46, (2004).
Levine et al., "Determination of Carbonyl Content in Oxidatively Modified Proteins," Methods in Enzymology, vol. 186, pp. 464-478, (1990).
Hagerhall et al., "Structure model for the membrane-integral domain of succinate: Quinone oxidoreductases," FEBS Letter, vol. 389, pp. 25-31, (1996).
Vibat, "Localization of Histidine Residues Responsible for Heme Axial Ligation in Cytochrome *b*556 of Complex II (Succinate: Ubiquinone Oxidoreductase) in *Escherichia coli*," Biochemistry, vol. 37, pp. 4148-4159, (1998).
Scheffler, "Molecular Genetics of Succinate: Quinone Oxidoreductase in Eukaryotes," Progress in Nucleic Acid Research and Molecular Biology, vol. 60, pp. 267-315, (1998).
Ackrell, "Progress in Understanding structure—function relationships in respiratory chain complex II," FEBS Letters, vol. 466, pp. 1-5, (2000).
Nakada et al., "Correlation of Functional and Ultrastructural Abnormalities of Mitochondria in Mouse Heart Carrying a Pathogenic Mutant mtDNA with a 4696-bp Deletion," Biochemical and Biophysical Research Communications, vol. 288, pp. 901-907, (2001).
Stadtman, "Protein Oxidation in Aging and Age-Related Diseases," Annals New York Academy of Sciences, vol. 928, pp. 22-38, (2001).
Toyokuni, "Reactive oxygen species-induced molecular damage and its application in pathology," Pathology International, vol. 49, pp. 91-102, (1999).
Cooke et al., "Oxidative DNA damage: mechanisms, mutation, and disease," FASEB Journal, vol. 17, pp. 1195-1214, (2003).
Marnett, "Oxyradicals and DNA damage," Carcinogenesis, vol. 21, pp. 361-370, (2000).
Kasai, "Analysis of a form of oxidative DNA damage, 8-hydroxy-2'-deoxyguanosine, as a marker of cellular oxidative stress during carcinogenesis," Mutation Research, vol. 387, pp. 147-163, (1997).

Knaap et al., "A Mutational Assay system for L5178Y mouse lymphoma cells, using hypoxanthine-guanine-phosphoribosyltransterase (HGPRT)—deficiency as marker. The occurrence of a long expression time for mutations induced by x-rays and EMS," Mutation Research, vol. 30, pp. 97-110, (1975).
Tsutsui et al., "Comparison between mutagenesis in normal and transformed Syrian hamster fibroblasts," Mutation Research, vol. 80, pp. 357-371, (1981).
Griparic et al., "The many shapes of Mitochondrial membranes," Traffic, vol. 2, pp. 235-244, (2001).
Westermann, "Merging mitochondria matters," EMBO reports, vol. 3, No. 6, pp. 527-531, (2002).
Mozdy et al., "A Fuzzy mitochondrial fusion apparatus comes into focus," Nature Reviews: Molecular Cell Biology, vol. 4, 468-478, (2003).
Kroemer et al., "The mitochondrial death/life regulator in apoptosis and necrosis," Annual Review of Physiology, vol. 60, pp. 619-642, (1998).
Zimmermann et al., "The Machinery of programmed cell death," Pharmacology & Therapeutics, vol. 92, pp. 57-70, (2001).
Degen et al., "Caspase-dependent cleavage of nucleic acid," Cell Death and Differentiation, vol. 7, pp. 616-627, (2000).
Robertson et al., "Review: Nuclear Events in Apoptosis," Journal of Structural Biology, vol. 129, pp. 346-358, (2000).
Wakabayashi, "Structural changes of mitochondria related to apoptosis: Swelling and megamitochondria formation," Acta Biochimica Polonica, vol. 46, No. 2, pp. 223-237, (1999).
Thress et al., "Mitochondria at the Crossroad of Apoptotic Cell Death," Journal of Bioenergetics and Biomembranes, col. 31, No. 4, pp. 321-326, (1999).
Budihardjo et al., "Biochemical pathways of caspase activation during apoptosis," Annu. Rev. Cell Dev. Biol. vol. 15, pp. 269-290, (1999).
Porter et al., "Emerging roles of caspase-3 in apoptosis," Cell Death and Differentiation, vol. 6, pp. 99-104, (1999).
Olinski et al., "Oxidative DNA base modifications as factors in carcinogenesis," Acta Biochimica Polonica, vol. 45, No. 2, pp. 561-572, (1998).
Kang, "Oxidative Stress, DNA Damage, and Breast Cancer," AACN Clinical Issues, vol. 13, No. 4, pp. 540-549, (2002).
Colburn et al., "Correlation of Anchorage-independent Growth with Tumorigenicity of chemically transformed mouse epidermal cells," Cancer Research, vol. 38, pp. 624-634, (1978). A.
Suh et al., "Cell Transformation by the superoxide-generating oxidase Mox1," Nature, vol. 401, pp. 79-82, (1999).

* cited by examiner

| | | | | | | | |
|---|---|---|---|---|---|---|---|
| *E.coli* | 1 | MI-------- | ---------- | ---------- | ---------- | ---------- | 50 |
| *C.elegans* | 1 | MINIPTAILC | RLGARSSISR | SFGTSIVTKS | E------AKT | PIQKFGWEYL | 50 |
| *Mus musculus* | 1 | M----AAFLL | RHVSRHCLRA | HENAQLCIRN | AAPLGTTAKE | EMERF-WK-- | 50 |
| *Bos taurus* | 1 | M----AALLL | RHVGRHCLRA | HLSPQLCIRN | AVPLGTTAKE | EMERF-WS-- | 50 |
| *Homo sapiens* | 1 | M----AALLL | RHVGRHGLRA | HFSPQLCIRN | AVPLGTTAKE | EMERE-WN-- | 50 |
| *E.coli* | 51 | -RNVKKQRPV | NLDLQTIRFP | ITAIASILHR | VSGVITFVAV | GILLWLLGTS | 100 |
| *C.elegans* | 51 | LKQRSKNRPI | APHLTVYQPQ | LTWMLSGFHR | ISGCV--MAG | TLLVGGIGFA | 100 |
| *Mus musculus* | 51 | -KNTSSNRPL | SPHLTIYKWS | LPMALSVCHR | GSGIA--LSG | GVSLFGLSAL | 100 |
| *Bos taurus* | 51 | -KNTTLNRPL | SPHISIYGWS | LPMAMSICHR | GTGIA--LSA | GVSLFGLSAL | 100 |
| *Homo sapiens* | 51 | -KNIGSNRPL | SPHITIYSWS | LPMAMSICHR | GTGIA--LSA | GVSLFGMSAL | 100 |
| *E.coli* | 101 | LSSPEGFEQA | SAI-----MG | SFFVKFIMWG | ILTALAYHVV | VGIRHMMMDF | 150 |
| *C.elegans* | 101 | VL-PFDFTAF | VDFIRSWNLP | CAVTAVFKYI | IAFPIIFHTL | NGIRFLGFDL | 150 |
| *Mus musculus* | 101 | VL-PGNFESY | LMFVKSLGLG | PTLIYSAKFV | LVFPLMYHSL | NGIRHLLWDL | 150 |
| *Bos taurus* | 101 | LV-PGSFESH | LEFVKSLCLG | PALIHTAKFA | LVFPLMYHTW | NGIRHLMWDL | 150 |
| *Homo sapiens* | 101 | LL-PGNFESY | LELVKSLGLG | PALIHTAKFA | LVFPLMYHTW | NGIRHLMWDL | 150 |
| *E.coli* | 151 | GYLEETFEAG | KRSAKISFVI | TVVLSLLAGV | LVW------- | ---------- | 200 |
| *C.elegans* | 151 | A---KGVNNV | GQIYKSGYLV | SGLSAILALA | IVFNSCQNKS | NKTA------ | 200 |
| *Mus musculus* | 151 | G---KGLA-I | PQVWLSGVA | VVLAVLSSGG | LA-------- | --AL------ | 200 |
| *Bos taurus* | 151 | G---KGLT-I | SQLHQSGVAV | LVLTVLSSVG | LA-------- | --AM------ | 200 |
| *Homo sapiens* | 151 | G---KGLK-I | PQLYQSGVVV | LVLTVLSSMG | LA-------- | --AM------ | 200 |

FIG. 1A

SEQUENCE LISTING

```
<160> NUMBER OF SEQ ID NOS: 26

<210> SEQ ID NO 1
<211> LENGTH: 169
<212> TYPE: PRT
<213> ORGANISM: Mouse

<400> SEQUENCE: 1

Met Ala Ala Phe Leu Leu Arg His Val Ser Arg His Cys Leu Arg Ala
1               5                   10                  15

His Leu Asn Ala Gln Leu Cys Ile Arg Asn Ala Ala Pro Leu Gly Thr
            20                  25                  30

Thr Ala Lys Glu Glu Met Glu Arg Phe Trp Lys Lys Asn Thr Ser Ser
        35                  40                  45

Asn Arg Pro Leu Ser Pro His Leu Thr Ile Tyr Lys Trp Ser Leu Pro
    50                  55                  60

Met Ala Leu Ser Glu Cys His Arg Gly Ser Gly Ile Ala Leu Ser Gly
65                  70                  75                  80

Gly Val Ser Leu Phe Gly Leu Ser Ala Leu Val Leu Pro Gly Asn Phe
                85                  90                  95

Glu Ser Tyr Leu Met Phe Val Lys Ser Leu Cys Leu Gly Pro Thr Leu
            100                 105                 110

Ile Tyr Ser Ala Lys Phe Val Leu Val Phe Pro Leu Met Tyr His Ser
        115                 120                 125

Leu Asn Gly Ile Arg His Leu Leu Trp Asp Leu Gly Lys Gly Leu Ala
    130                 135                 140

Ile Pro Gln Val Trp Leu Ser Gly Val Ala Val Val Val Leu Ala Val
145                 150                 155                 160

Leu Ser Ser Gly Gly Leu Ala Ala Leu
                165


<210> SEQ ID NO 2
<211> LENGTH: 510
<212> TYPE: DNA
<213> ORGANISM: Mouse

<400> SEQUENCE: 2
```

-continued

```
atggctgcgt tcttgctgag acatgtcagc cgtcactgcc tccgagccca cctgaatgct     60

cagctttgta tcagaaatgc tgctcctttg ggaaccacag ctaaggagga gatggagcgg    120

ttctggaaga agaacacgag ttcaaaccgt cctctgtctc cccatttgac tatctacaaa    180

tggtctcttc ccatggcact gtccgaatgc caccgaggct ctggaatagc cttgagtgga    240

ggggtctctc tttttggcct gtcggcactg gtgcttcctg ggaactttga gtcgtatttg    300

atgtttgtga agtccctgtg tttggggcca acactgatct actcggctaa gtttgtgctt    360

gtcttcccgc tcatgtacca ctcactgaat gggatccgac acttgctatg ggacctagga    420

aaaggcctgg caatacccca ggtctggctg tctggagtgg cggtcgtggt tcttgctgtg    480

ttgtcctctg gcgggctggc cgccctgtga                                     510


<210> SEQ ID NO 3
<211> LENGTH: 36
<212> TYPE: DNA
<213> ORGANISM: Artificial
<220> FEATURE:
<223> OTHER INFORMATION: primer

<400> SEQUENCE: 3

ggggaattca tggctttctt gctgagacat gtcagc                               36


<210> SEQ ID NO 4
<211> LENGTH: 27
<212> TYPE: DNA
<213> ORGANISM: Artificial
<220> FEATURE:
<223> OTHER INFORMATION: primer

<400> SEQUENCE: 4

gggaagcttt cacagggcgg ccagccc                                         27


<210> SEQ ID NO 5
<211> LENGTH: 36
<212> TYPE: DNA
<213> ORGANISM: Artificial
<220> FEATURE:
<223> OTHER INFORMATION: primer

<400> SEQUENCE: 5

ggggaattcc tcttcccatg gcactgtccg aatgcc                               36


<210> SEQ ID NO 6
<211> LENGTH: 27
<212> TYPE: DNA
<213> ORGANISM: Artificial
<220> FEATURE:
<223> OTHER INFORMATION: primer

<400> SEQUENCE: 6

gggaagcttt cacagggcgg ccagccc                                         27


<210> SEQ ID NO 7
<211> LENGTH: 45
<212> TYPE: DNA
<213> ORGANISM: Artificial
<220> FEATURE:
<223> OTHER INFORMATION: primer

<400> SEQUENCE: 7

gggggtacca atattgctag cgagcttggc ccattgcata cgttg                     45
```

-continued

```
<210> SEQ ID NO 8
<211> LENGTH: 60
<212> TYPE: DNA
<213> ORGANISM: Artificial
<220> FEATURE:
<223> OTHER INFORMATION: primer

<400> SEQUENCE: 8

gggctcgagc acgtgaagct tcggatccga attcgctagc ggggccgcgg aggctggatc     60


<210> SEQ ID NO 9
<211> LENGTH: 21
<212> TYPE: DNA
<213> ORGANISM: Artificial
<220> FEATURE:
<223> OTHER INFORMATION: primer

<400> SEQUENCE: 9

gggggatcca gacatgataa g                                               21


<210> SEQ ID NO 10
<211> LENGTH: 39
<212> TYPE: DNA
<213> ORGANISM: Artificial
<220> FEATURE:
<223> OTHER INFORMATION: primer

<400> SEQUENCE: 10

gggggtaccg ggcccagatc tggtcgagct gatacttcc                            39


<210> SEQ ID NO 11
<211> LENGTH: 33
<212> TYPE: DNA
<213> ORGANISM: Artificial
<220> FEATURE:
<223> OTHER INFORMATION: primer

<400> SEQUENCE: 11

ggggaattca agcttggcgg tggtgctttg tct                                  33


<210> SEQ ID NO 12
<211> LENGTH: 40
<212> TYPE: DNA
<213> ORGANISM: Artificial
<220> FEATURE:
<223> OTHER INFORMATION: primer

<400> SEQUENCE: 12

gggggatcct taaactgatg atttgatttc aaatgcagtc                           40


<210> SEQ ID NO 13
<211> LENGTH: 48
<212> TYPE: DNA
<213> ORGANISM: Artificial
<220> FEATURE:
<223> OTHER INFORMATION: primer

<400> SEQUENCE: 13

ggggaattcg ccgccaccat ggctgcgttc ttgctgagac atgtcagc                  48


<210> SEQ ID NO 14
<211> LENGTH: 36
<212> TYPE: DNA
<213> ORGANISM: Artificial
<220> FEATURE:
<223> OTHER INFORMATION: primer
```

-continued

<400> SEQUENCE: 14
gggaagcttt ctagaaaatc acagggcggc cagccc 36

<210> SEQ ID NO 15
<211> LENGTH: 36
<212> TYPE: DNA
<213> ORGANISM: Artificial
<220> FEATURE:
<223> OTHER INFORMATION: primer

<400> SEQUENCE: 15
ggggaattcc tcttcccatg gcactgtccg aatgcc 36

<210> SEQ ID NO 16
<211> LENGTH: 36
<212> TYPE: DNA
<213> ORGANISM: Artificial
<220> FEATURE:
<223> OTHER INFORMATION: primer

<400> SEQUENCE: 16
gggaagcttt ctagaaaatc acagggcggc cagccc 36

<210> SEQ ID NO 17
<211> LENGTH: 29
<212> TYPE: DNA
<213> ORGANISM: Artificial
<220> FEATURE:
<223> OTHER INFORMATION: primer

<400> SEQUENCE: 17
ggggatatcg ggacagcccc cccccaaag 29

<210> SEQ ID NO 18
<211> LENGTH: 28
<212> TYPE: DNA
<213> ORGANISM: Artificial
<220> FEATURE:
<223> OTHER INFORMATION: primer

<400> SEQUENCE: 18
ggggatatcc tcactgactc cgtcctgg 28

<210> SEQ ID NO 19
<211> LENGTH: 81
<212> TYPE: DNA
<213> ORGANISM: Artificial
<220> FEATURE:
<223> OTHER INFORMATION: primer

<400> SEQUENCE: 19
gggtctagaa atattaagct ttgcggccgc atgcccaaga agaagcgcaa ggtggaggac 60
gccatggtga gcaagggcga g 81

<210> SEQ ID NO 20
<211> LENGTH: 42
<212> TYPE: DNA
<213> ORGANISM: Artificial
<220> FEATURE:
<223> OTHER INFORMATION: primer

<400> SEQUENCE: 20
gggggtaccg ggccccggat cccttgtaca gctcgtccat gc 42

-continued

<210> SEQ ID NO 21
<211> LENGTH: 27
<212> TYPE: DNA
<213> ORGANISM: Artificial
<220> FEATURE:
<223> OTHER INFORMATION: primer

<400> SEQUENCE: 21
gggggatcca tggaagacgc caaaaac 27

<210> SEQ ID NO 22
<211> LENGTH: 35
<212> TYPE: DNA
<213> ORGANISM: Artificial
<220> FEATURE:
<223> OTHER INFORMATION: primer

<400> SEQUENCE: 22
gggggtaccg ggcccttaca atttggactt tccgc 35

<210> SEQ ID NO 23
<211> LENGTH: 31
<212> TYPE: DNA
<213> ORGANISM: Artificial
<220> FEATURE:
<223> OTHER INFORMATION: primer

<400> SEQUENCE: 23
gggtctagag cctctgctaa ccatgttcat g 31

<210> SEQ ID NO 24
<211> LENGTH: 39
<212> TYPE: DNA
<213> ORGANISM: Artificial
<220> FEATURE:
<223> OTHER INFORMATION: primer

<400> SEQUENCE: 24
ggggaatccg aattctttgc caaaatgatg agacagcac 39

<210> SEQ ID NO 25
<211> LENGTH: 35
<212> TYPE: DNA
<213> ORGANISM: Artificial
<220> FEATURE:
<223> OTHER INFORMATION: primer

<400> SEQUENCE: 25
gggggatcct acgtatcgag gtgagcccca cgttc 35

<210> SEQ ID NO 26
<211> LENGTH: 35
<212> TYPE: DNA
<213> ORGANISM: Artificial
<220> FEATURE:
<223> OTHER INFORMATION: primer

<400> SEQUENCE: 26
ggggaattct ctagagccgc cggtcacgcc agaag 35

TRANSGENIC CELL AND GENE RECOMBINANT ANIMAL HAVING A MUTANT SDHC GENE DERIVED FROM MAMMALS

TECHNICAL FIELD

The present invention relates to a transgenic cell and a gene recombinant animal having a mutant SDHC gene derived from mammals. More specifically, the present invention relates to a transgenic cell and a gene recombinant animal, which are characterized in that they have a mutant SDHC gene and causes apoptosis or cancerogenesis in response to oxidation stress.

BACKGROUND ART

Major endogenous reactive oxygen species (ROS) result from electron leakage through electron transport in mitochondria (Cadenas, E. et al., (2000) Free. Radic. Biol. Med. 29, 222-230; Lenaz, G. (2001) IUBMB Life. 52, 159-164; Chen, Q. et al., (2003) J. Biol. Chem. 278, 36027-36031; Turrens, J. F. (1997) Biosci. Rep. 17, 3-8; and Liu, S. S. (1999) J. Bioenerg. Biomembr. 31, 367-376). It is believed that excessive ROS results in induction of apoptosis or cancer (Jacobson, M. D. (1996) Trends. Biochem. Sci. 21, 83-86; Mignotte, B. et al., (1998) Eur. J. Biochem. 252, 1-15; Floyd, R. A. (1990) FASEB J. 4, 2587-2597; Cerutti, P. A. et al., (1991) Cancer Cell. 3, 1-7; and Kovacic, P et al., (2001) Curr. Med. Chem. 8, 773-796), but direct evidence is somewhat lacking. Many researchers who study oxidative stress resort to either the chemical production of ROS in cells using drugs such as paraquat (Hassan, H. M. et al., (1979) J. Biol. Chem. 254, 10846-10852; and Feng, J. et al., (2001) Dev. Cell. 1, 633-644) or the use of electron transport inhibitors so as to increase endogenous production of free radicals (Aitken, R. J. et al., (1997) Mol. Reprod. Dev. 47, 468-482; and Saybasili, H. et al., (2001) Antioxid. Redox. Signal. 3, 1099-1104). However, these drugs also pose severe cellular toxicity and therefore such studies may not provide accurate portrayals of the deleterious effects of natural endogenous ROS from mitochondria. So as to avoid this pitfall, the present inventors have previously isolated a mutant of *C. elegans*, mev-1 (kn1) (Ishii, N. et al., (1990) Mutat. Res. 237, 165-171), which has a genetic dysfunction in electron transport and therefore overproduces ROS in its mitochondria (Senoo-Matsuda, et al., (2001) J. Biol. Chem. 276, 41553-41558). This gene encodes Cyt-1, which is homologous to SDHC in humans and is one subunit of complex II (Ishii, N. et al., (1998) Nature 394, 694-697). The kn1 mutation leads to apoptosis and precocious aging in *C. elegans* (Senoo-Matsuda, et al., (2003) J. Biol. Chem. 278, 22031-22036; Honda, S, et al., (1993) J. Gerontol. 48. B57-61; and Hosokawa, H. et al., (1994) Mech. Ageing. Dev. 74, 161-170).

DISCLOSURE OF THE INVENTION

It is an object of the present invention to provide a transgenic cell and gene recombinant animal having a mutant SDHC gene, which enables the examination of the action of reactive oxygen species (ROS) derived from mitochondria in mammals.

As a result of intensive studies directed towards achieving the aforementioned object, the present inventors have succeeded in establishing a transgenic mouse fibroblast NIH3T3 cell line, into which an SDHC gene having a mutation equivalent to that of mev-1 of *C. elegans* has been introduced. The ROS superoxide anion ($O_2^-$) was overproduced in the produced transgenic cell lines, resulting in more cellular damage than in the isogenic wild-type cell line. The resultant oxidative stress induced many apoptotic cells. Moreover, the cells that escaped apoptosis were frequently transformed. Recently it is found that a mutation of the SDHC gene causes some familial chromaffin cell tumors (i.e., paragangliomas) (Niemann, S et al., (2000) Nature genet. 26, 268-270) in humans. These evidences show that ROS from mitochondria is related to not only apoptosis but also tumorigenesis. The present invention has been made based on these findings.

That is to say, the present invention provides the following invention.

(1) A transgenic animal cell, which is characterized in that a mutant SDHC gene derived from mammals is introduced into the cell, and that reactive oxygen species (ROS) are excessively produced in the cell.

(2) The transgenic animal cell according to (1) above, wherein, in the above mutant SDHC gene, an amino acid residue in a protein encoded by an SDHC gene, which corresponds to glycine, an amino acid residue at position 71 in a protein encoded by the cyt-1 gene of *C. elegans*, is substituted by glutamic acid or aspartic acid.

(3) The transgenic animal cell according to (1) or (2) above, wherein the mutant SDHC gene derived from mammals is an SDHC gene derived from mice.

(4) The transgenic animal cell according to any one of (1) to (3) above, wherein the protein encoded by the mutant SDHC gene derived from mice is a protein having the amino acid sequence shown in SEQ ID NO: 1 in the sequence listing.

(5) The transgenic animal cell according to any one of (1) to (4) above, wherein apoptosis is induced at a greater level than that in a wild-type cell.

(6) The transgenic animal cell according to any one of (1) to (5) above, which has a higher tumorigenesis ability than that of a wild-type cell.

(7) A gene recombinant non-human mammal or a portion thereof, which is characterized in that a mutant SDHC gene derived from mammals is introduced therein, and that reactive oxygen species (ROS) are excessively produced therein.

(8) The gene recombinant non-human mammal or a portion thereof according to (7) above, wherein, in the above mutant SDHC gene, an amino acid residue in a protein encoded by an SDHC gene, which corresponds to glycine, an amino acid residue at position 71 in a protein encoded by the cyt-1 gene of *C. elegans*, is substituted by glutamic acid or aspartic acid.

(9) The gene recombinant non-human mammal or a portion thereof according to (7) or (8) above, wherein the mutant SDHC gene derived from mammals is a mutant SDHC gene derived from mice.

(10) The gene recombinant non-human mammal or a portion thereof according to any one of (7) to (9) above, wherein the protein encoded by the mutant SDHC gene derived from mice is a protein having the amino acid sequence shown in SEQ ID NO: 1 in the sequence listing.

(11) The gene recombinant non-human mammal or a portion thereof according to any one of (7) to (10) above, wherein apoptosis is induced at a greater level than that in a wild-type mammal.

(12) The gene recombinant non-human mammal or a portion thereof according to any one of (7) to (11) above, which has a higher tumorigenesis ability than that of a wild-type mammal.

(13) A gene-introducing vector for the production of the transgenic animal cell according to any one of (1) to (6) above or the gene recombinant non-human mammal according to any one of (7) to (12) above, which comprises a gene encoding a protein having the amino acid sequence shown in SEQ ID NO: 1 in the sequence listing.

(14) A method for screening for a substance having action to suppress excessive reactive oxygen species (ROS), which is characterized in that the transgenic animal cell according to any one of (1) to (6) above, or the gene recombinant non-human mammal or a portion thereof according to any one of (7) to (12) above is used.

(15) The screening method according to (14) above, wherein the substance having action to suppress excessive reactive oxygen species (ROS) is an apoptosis inhibitor or anticancer agent.

Figure 1B:
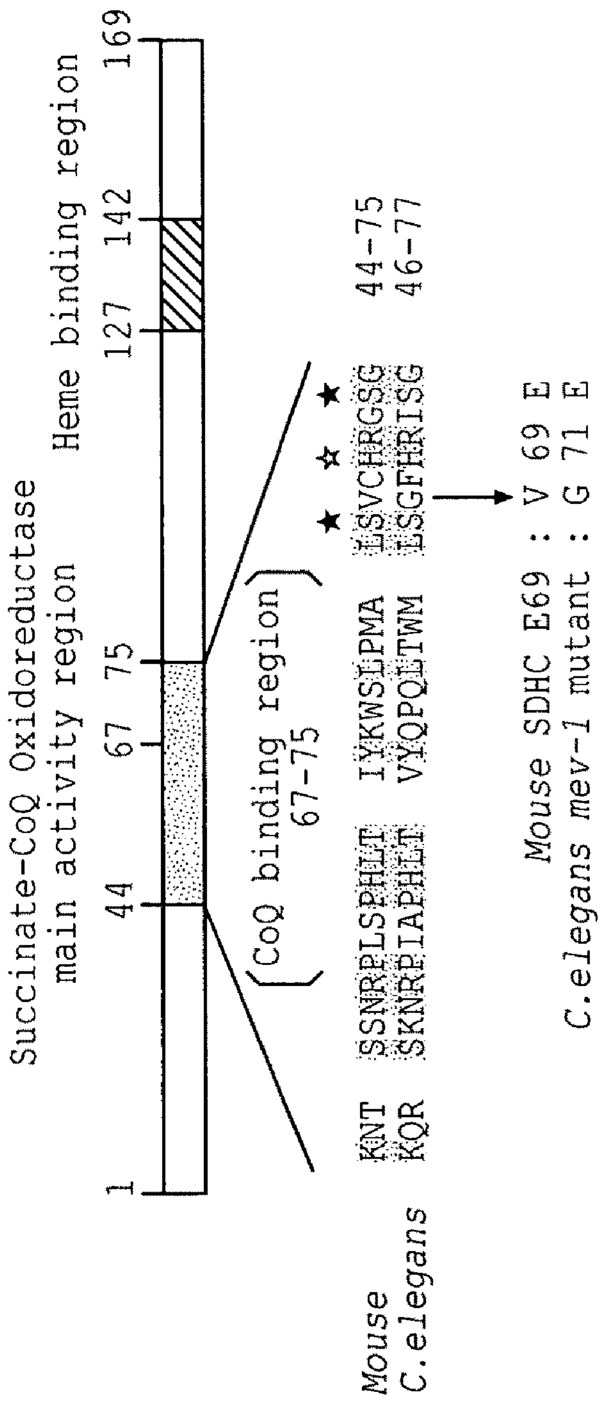
FIG. 1 shows sequence comparisons and structure of the SDHC gene as well as the construction of the mutant SDHC transgene.

A, The deduced amino-acid sequences of SDHC from *E. coli, C. elegans* (CYT-1), *Mus musculus, Bos taurus* (CII-3) and *Homo sapiens* SDHC. The dark shaded boxes indicate identical residues.

B, Overall structure of the mouse SDHC protein. It consists of 169 amino-acids, of which the 44-75 amino-acid region is the deduced succinate-CoQ oxidoreductase main active site, the 67-75 region is a CoQ-binding site and the 127-142 region is a Heme-binding site, respectively. The mev-1/CYT-1 missense mutation of *C. elegans* mev-1 results in a glycine to glutamic acid substitution at residue 71. The two serines in both the mouse and *C. elegans* sequences (closed asterisks) in a CoQ-binding region are nucleophilic residues, and histidine (open asterisk) is the main residue of CoQ-binding site.

C, Construction of the mev-1 mutant-type mouse SDHC transgene. As the thymine residues of 206 and 207 in the DNA sequence were changed to adenines, the valine at 69 in the amino acid sequence was changed to glutamic acid (SDHC Val69Glu). In addition, to distinguish mutant and wild-type alleles, a cutting site of NcoI restriction enzyme was created by a thymine-to-cytosine substitution at position 192.

D, RT-PCR analysis of the SDHC gene expression in SDHC E69 mutant cell lines. The wild-type (WT) and mutant SDHC PCR products from each cell extract were treated with NcoI restriction enzyme so as to distinguish them.

FIG. 2 shows $O_2^-$ production from mitochondria in SDHC E69 mutant cell lines. WT: wild type.

A, Measurements of activities of Complex I (closed boxes) and Complex II (hatched boxes). *: p<0.01.

B, $O_2^-$ production from mitochondria in vitro. *: p<0.05.

C, Effect of $CoQ_{10}$. *: p<0.01; closed boxes: control; hatched boxes: CoQ medium.

D, Accumulation of $O_2^-$ in mitochondria in vivo. *: p<0.01; **: p=0.067.

FIG. 3 shows the measurement of intracellular oxidative stress in SDHC E69 mutant cell lines. WT: wild type.

A and B, Measurements of protein carbonyls by a Dot blot analysis using anti-DNPH antibodies. The protein carbonyls were obtained from cytosolic fractions (A) (*: p<0.01) and membrane fractions (B) (*: p<0.01), respectively.

C, Measurement of 8-OHdG by a direct immuno-fluorescence analysis (flow-cytometery) using the FITC-Conjugate antibody in Oxidative DNA Damage Assay Kit (KAMIYA Biomedical company).

D, Measurement of 6-Thioguanine (6-TG) resistance cells in wild-type cells (●), one-month (¦) and three-month (▲) SDHC E69 mutant cell lines (*: p<0.01).

E, Measurement of mutation frequencies in the nuclear gene hypoxanthine phosphoribosyl transferase (hprt). The wild-type cells and one-month SDHC E69 mutant cell lines were cultured in 6 μM of 6-TG containing medium and three-month SDHC E69 mutant cells were cultured in 12 μM. The survival rates of wild-type cells and one-month and three-month SDHC E69 mutant cells were equivalent at these doses. *: p<0.01.

FIG. 4 shows morphology of mitochondria and mitochondria membrane potential in SDHC E69 cell lines. WT: wild type.

A and B, Morphological observations of the wild-type cells (for 3 month cultured cells) and one-month and three-month SDHC E69 mutant cell lines with electron microscopy (scale bar=10 μm).

C and D, Measurements of mitochondrial membrane potential ($\Delta\Psi_m$) by JC-1 (5,5',6,6'-tetrachloro-1,1',3,3'-tetraethylbenzimidazolocarbocyanine iodide) (Molecular Probes Company). JC-1 is a J-aggregate-forming lipophilic cation. In cells, green fluorescence indicates lipoprotein in mitochondrial membrane (C) and red fluorescence reflects mitochondria membrane potential (data not shown). Yellow color is shown by the merger of red and green fluorescence, which indicates the ratio of strength of mitochondria membrane potential relative to lipoprotein amounts (D).

FIG. 5 shows morphology and cell division and proliferation of SDHC E69 mutant cell lines.

A, Morphologies of the confluent wild-type cells (WT) (for 3 month cultured cells) and one-month and three-month SDHC E69 mutant cell lines (original magnification: 100×; upper panel, 40×; lower panel). There were no observable morphological changes in the wild-type cells during the three month culture period. The white arrows indicate some apoptotic molecule-like granules that resulted from apoptosis.

B, Cell division and proliferation of wild-type cells (●), one-month (¦) and three-month (▲) SDHC E69 mutant cell lines (*: p<0.01).

FIG. 6 shows apoptosis induction and transformation of SDHC E69 cell lines. WT: wild type.

A, Measurement of CPP32/Caspase 3 activity by DEVD (Asp-Glu-Val-Asp)-pNA (p-nitroanilide) substrate using CPP32/Caspase 3 Colorimetric Protease Assay Kit (MBL Company) (*: p<0.01).

B, Detection of DNA fragmentations in one-month and three-month SDHC E69 mutant cell lines by gel electrophoresis and ethidium bromide staining.

C, Phagocytosis and tumorgenesis on epithelia of nude mice. One million cells were injected subcutaneously at several sites.

D, Anchorage-independent growth in soft-agar medium. These cells were cultured in the medium for one and a half month after inoculation.

Figure 7:
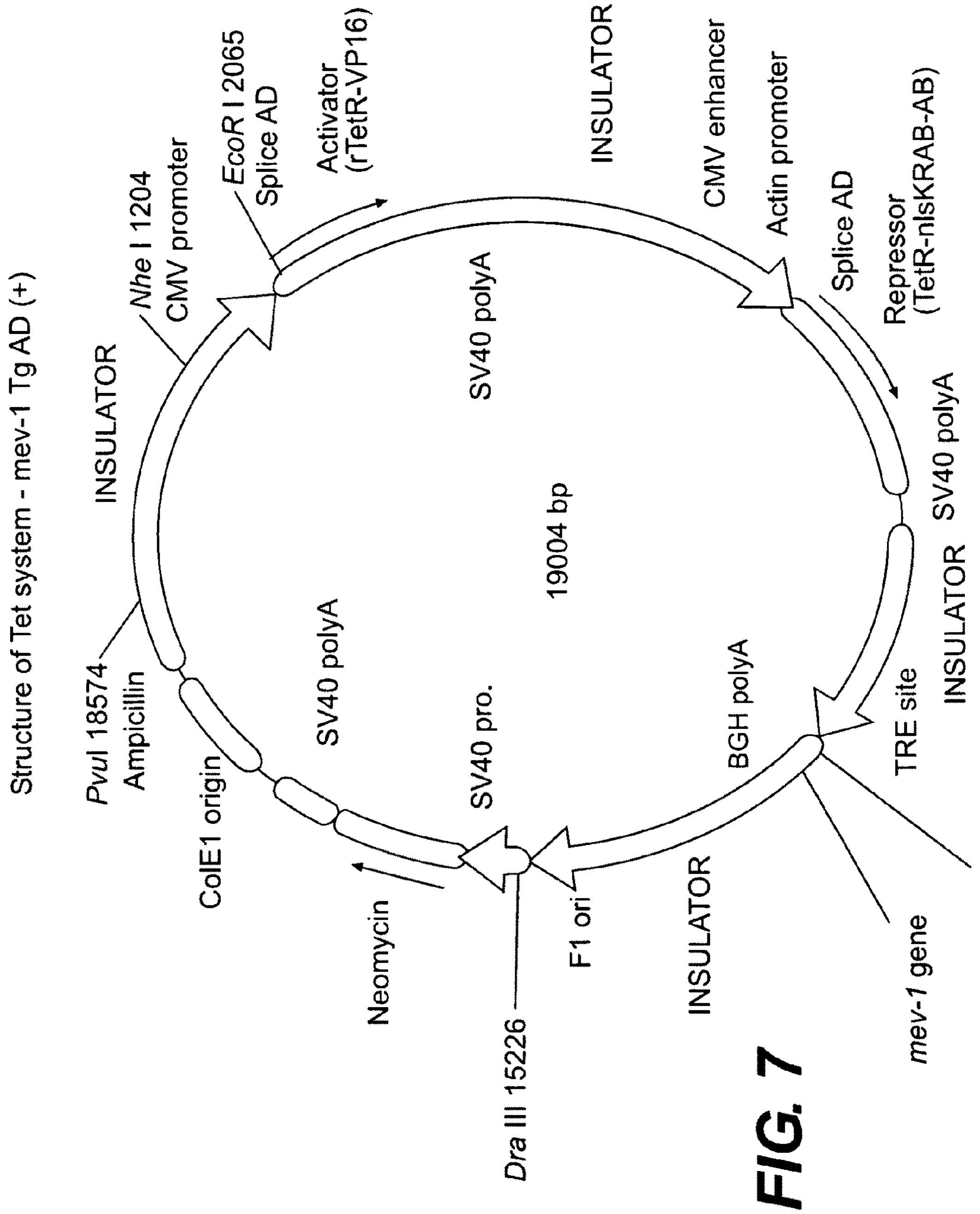

FIG. 7 shows a summary of Tet system-mev-1 Tg AD (+).

Figure 8:
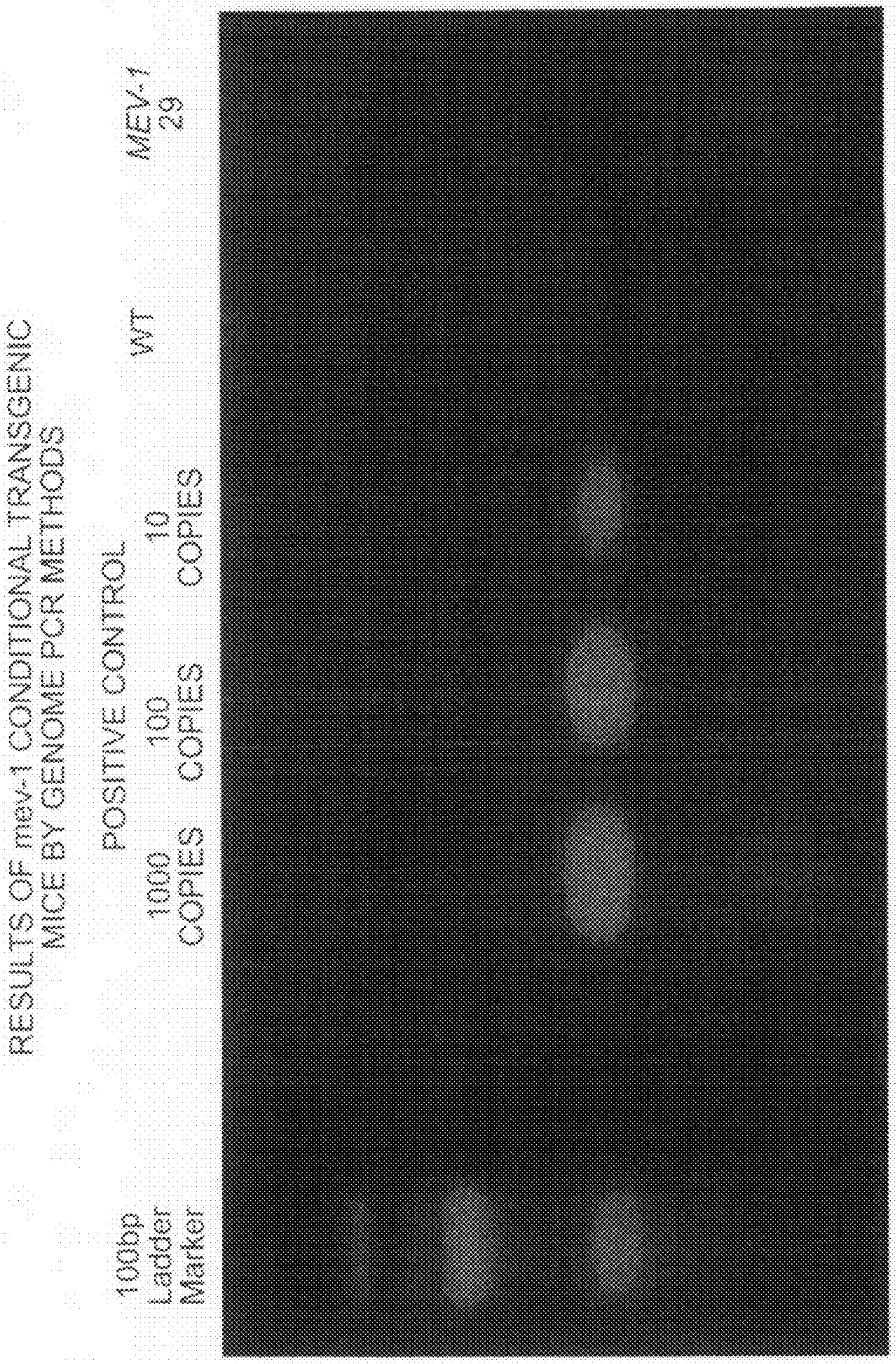

FIG. 8 shows the results obtained by extracting genomic DNA from the tail of a mev-1 conditional transgenic mouse and then amplifying a mev-1 cyt-1 gene contained in a transgene by the PCR method.

BEST MODE FOR CARRYING OUT THE INVENTION

The embodiments of the present invention will be described below.

(1) Transgenic Animal Cell of the Present Invention

The transgenic animal cell of the present invention is a cell characterized in that a mutant SDHC gene derived from mammals is introduced therein, and that reactive oxygen species (ROS) are excessively produced therein. The transgenic animal cell of the present invention is further characterized in that, as a result of excessive production of reactive oxygen species (ROS), preferably, apoptosis is induced at a greater level than that of a wild-type cell, or the tumorigenesis ability thereof is increased when compared with a wild-type cell.

Any mutant SDHC gene may be used in the present invention, as long as it is derived from mammals, and the origin thereof is not particularly limited. Examples of such a mutant SDHC gene may include mutant SDHC genes derived from rodents such as a mouse, hamster, Guinea pig, rat, or rabbit, and mutant SDHC genes derived from a chicken, dog, cat, goat, sheep, bovine, swine, monkey, or human. Of these, the mutant SDHC genes derived from rodents such as a mouse, hamster, Guinea pig, rat, or rabbit are preferably used. In particular, a mutant SDHC gene derived from a mouse is most preferable.

SDHC genes derived from mammals are known.

For example, the followings can be used:

mouse: BC005779 (NCBI) (reference; Strausberg, R. L., et al., Generation and initial analysis of more than 15,000 full-length human and mouse cDNA sequences, Proc. Natl. Acad. Sci. U.S.A. 99 (26), 16899-16903 (2002)), and NM_025321 (NCBI) (reference Paddenberg, R., et al., Essential role of complex II of the respiratory chain in hypoxia-induced ROS generation in the pulmonary vasculature, Am. J. Physiol. Lung Cell Mol. Physiol. 284 (5), L710-L719 (2003))

bovine: NM_175814(NCBI)(reference; Yu, L., et al., Cytochrome b560 (QPs1) of mitochondrial succinate-ubiquinone reductase. Immunochemistry, cloning, and nucleotide sequencing, J. Biol. Chem. 267 (34), 24508-24515 (1992)

swine: AJ300475(NCBI) (reference; Stratil, A., et al., Linkage and radiation hybrid mapping of the porcine gene for subunit C of succinate dehydrogenase complex (SDHC) to chromosome 4, Anim. Genet. 32 (2), 110-112 (2001))

human: BC066329 (NCBI), BC033626 (NCBI) and BC020808 (NCBI) (reference; Strausberg, R. L., et al., Generation and initial analysis of more than 15,000 full-length human and mouse cDNA sequences, Proc. Natl. Acad. Sci. U.S.A. 99 (26), 16899-16903 (2002)), NM_003001 (NCBI) (reference; Niemann, S., et al., Autosomal dominant malignant and catecholamine-producing paraganglioma caused by a splice donor site mutation in SDHC, JOURNAL Hum. Genet. 113 (1), 92-94 (2003)), AF039589 (NCBI) (reference; Elbehti-Green, A., et al., Characterization of the human SDHC gene encoding of the integral membrane proteins of succinate-quinone oxidoreductase in mitochondria, Gene 213 (1-2), 133-140 (1998)), D49737 (NCBI) and AB006202 (NCBI) (reference Hirawake, H., et al., Cytochrome b in human complex II (succinate-ubiquinone oxidoreductase): cDNA cloning of the components in liver mitochondria and chromosome assignment of the genes for the large (SDHC) and small (SDHD) subunits to 1q21 and 11q23, Cytogenet. Cell Genet. 79 (1-2), 132-138 (1997)):

As a mutant SDHC gene used in the present invention, an SDHC gene comprising any mutation can be used, as long as it enables excessive production of reactive oxygen species (ROS) in mitochondria and also is not lethal to cells. In the present invention, the term "mutant SDHC gene" is used to mean a gene comprising a mutation (for example, a spontaneous mutation) in the DNA sequence of a wild-type SDHC gene. More specifically, the following can be used: a gene comprising a deletion of a portion of the nucleotide sequence of the wild-type SDHC gene; a gene comprising a substitution of a portion of the nucleotide sequence of the above gene by another nucleotide sequence; a gene comprising an insertion of another nucleotide sequence into a portion of the above gene; and so on. The number of nucleotides to be deleted, substituted, or added is not particularly limited. The number of such nucleotides is generally between 1 and 20, preferably between 1 and 10, more preferably between 1 and 5, particularly preferably between 1 and 3, and most preferably 1. Such a deletion, substitution, or addition of nucleotides results in a deletion, substitution, or addition of preferably 1 and 20, more preferably 10, further more preferably between 1 and 5, particularly preferably between 1 and 3, and most preferably 1 amino acid in the amino acid sequence of SDHC.

An example of such a mutant SDHC gene may be a mutant SDHC gene wherein an amino acid residue in a protein encoded by an SDHC gene, which corresponds to glycine, an amino acid residue at position 71 in a protein encoded by the cyt-1 gene that is a homolog in *C. elegans*, is substituted by glutamic acid or aspartic acid (particularly preferably, glutamic acid). An example of a protein encoded by the above mutant SDHC gene derived from mice may be a protein having the amino acid sequence shown in SEQ ID NO: 1 in the sequence listing. An example of a gene encoding the amino acid sequence shown in SEQ ID NO: 1 in the sequence listing is shown in SEQ ID NO: 2.

The aforementioned mutant SDHC gene can be obtained by genetic engineering techniques well known to a person skilled in the art, including production of primers, preparation of genomic DNA and cDNA, PCR, cloning, and enzyme treatment.

The transgenic animal cell of the present invention can be produced by introducing the above-described mutant SDHC gene derived from mammals into an animal cell.

A method for producing the transgenic animal cell of the present invention is not particularly limited. For example, it can be produced by introducing into an animal cell, an expression vector into which a mutant SDHC gene has been incorporated under the control of a promoter.

A transgene that is used to produce a transgenic animal cell is preferably a recombinant gene obtained by ligating the above-described mutant SDHC gene downstream of a suitable promoter used for mammals. Downstream of the above mutant SDHC gene, a poly A signal can also be ligated, as desired.

The type of a promoter used for mammals that is used to construct a transgene is not particularly limited. A promoter capable of allowing a mutant SDHC gene to express in an animal cell is preferably used. Specific examples of such a promoter may include gene promoters derived from viruses (for example, Cytomegalovirus, Moloney leukemia virus, JC virus, mammary tumor virus, etc.), promoters derived from various types of mammals (for example, a human, a rabbit, a dog, a cat, a Guinea pig, a hamster, a rat, a mouse, etc.), and promoters derived from Aves (for example, a chicken, etc.).

Moreover, a terminator necessary for the expression of a mutant SDHC gene may be ligated to the transgene which is used in the present invention. Such a terminator is used as a sequence for terminating the transcription of a messenger RNA of interest (what is called poly A) in a transgenic animal cell. The sequences of various genes derived from viruses, various types of mammals, and Aves can be used as such terminators. More specifically, a simian virus SV40 terminator or the like can be used. Furthermore, in order to allow the mutant SDHC gene to express at a higher level, the splicing signal or enhancer region of a known gene can also be ligated. Further, a portion of the intron of a eukaryotic gene can be ligated to the 5'-upstream of a promoter region, between a promoter region and a translation region, or to the 3'-downstream of a translation region.

The type of an animal cell used in the present invention is not particularly limited. Examples of such an animal cell used herein may include cells derived from rodents such as a mouse, hamster, Guinea pig, rat, or rabbit, and cells derived from a chicken, a dog, a cat, a goat, a sheep, a bovine, a swine, a monkey, a human, etc. It is preferable that a mutant SDHC gene to be introduced and a transgenic animal cell be derived from the same animal.

Examples of an animal cell to be used may include an endothelial cell, an epidermic cell, an islet, a cell derived from nerve tissues such as neuron, a mesothelial cell, an osteocyte, a lymphocyte, a chondrocyte, a hematopoietic cell, an immunocyte, a cell derived from various types of organs (for example, liver, lung, heart, stomach, spleen, kidney, skin, etc.), a muscle cell (including cells derived from skeletal muscle, smooth muscle, and cardiac muscle), an exocrine or endocrine cell, a fibroblast, and a totipotent or pluripotent stem cell of an embryo or the like. Moreover, various types of cell lines that have been established (for example, NIH3T3 cells, HEK293 cells, COS-1 cells, COS-7 cells, HeLa cells, Chinese hamster (CHO) cells, etc.) can also be used.

A mutant SDHC cell can be introduced into an animal cell by a common gene introduction method that is known to a person skilled in the art. Specific examples of such a gene introduction method may include electroporation, the calcium phosphate method, and lipofection.

In Examples that will be described later in the present specification, mouse fibroblast NIH3T3 cell lines that overproduce endogenous $O_2^-$ from mitochondria were established by transfecting NIH3T3 cells with a missense mutant of the SDHC gene. The mutation resulted in the substitution of glutamic acid for valine at position 69, which adjoins the serine residue in CoQ binding site (Yang, X. et al., (1998) J. Biol. Chem. 273, 31916-31923; and Yankovskaya, V. et al., (2003) Science 299, 700-704). It is thought that the serine residue is an active center of oxidoreductase and acts as nucleophilic amino acid. Furthermore, the substitution from an aliphatic to acidic amino acid may affect CoQ binding to the adjacent histidine (see the above references). This alternation would also be predicted to reduce complex II activity. It might also result in excess electron leakage from electron transport and thereby increase $O_2^-$ production. The data described in the Examples of the present invention are consistent with these predictions. It has been demonstrated by the present invention that a variety of pathologies (especially increased apoptosis, mutation and transformation) derive from the above mutation.

The mutation in the *C. elegans* mev-1 gene leads to apoptosis and precocious aging. In addition to these phenotypes, the same mutation in mouse SDHC E69 cells also leads to tumorigenesis. In humans, a mutation in complex II was found in patients of some familial chromaffin cell tumors (i.e., paragangliomas). The mouse cell line of the present invention has now enabled information as to the mechanism by which mitochondrial dysfunction causes carcinogenesis.

In the present invention, it has been shown that damage induced by oxidative stress can lead to apoptosis and tumorigenesis. However, these may ultimately play into different diseases. Specifically, while apoptosis may have evolved to act as a defense system against oxidative stress so as to rid organisms of badly damaged cells, excessive apoptosis very likely leads to neuronal degeneration and aging (Zhang, Y. et al., (2002) Mech. Ageing. Dev. 123, 245-260; Floyd, R. A. et al., (2002) Neurobiol. Aging 23, 795-807; Simonian, N. A. et al., (1996) Annu. Rev. Pharmacol. Toxicol. 36, 83-106; and Mattson, M. P. (2000) Natl. Rev. Mol. Cell. Biol. 1, 120-129). On the other hand, mutations can accumulate in those cells that escape apoptosis. As a result, the cells can become transformed. Melov and colleagues (Melov, S. (2000) Ann. N Y Acad. Sci. 908, 219-225; and Samper, E. et al., (2003) Aging Cell. 2, 277-285) have also demonstrated the deleterious consequences of ROS generation in mitochondria. Specifically, mice lacking the mitochondrial superoxide dismutase were shown to have elevated levels of oxidative damage to their nuclear DNA. This same mitochondrial defect results in a nine-fold increase in chromosome rearrangements. Thus, mitochondrial dysfunction can lead to DNA damage and mutation, events that can ultimately lead to apoptosis and transformation.

As a result of studies using the cell line of the present invention, it has been demonstrated that oxidation stress occurs as a result of generation of $O_2^-$ in mitochondria. Such oxidation stress is likely to bring on apoptosis, premature aging, and pathologic states such as neurodegeneration and cancerogenesis.

(2) Gene Recombinant Non-Human Mammal of the Present Invention

The gene recombinant non-human mammal of the present invention is characterized in that a mutant SDHC gene derived from mammals is introduced therein, and that reactive oxygen species (ROS) are excessively produced therein.

A method for producing a gene recombinant animal (for example, a transgenic animal) is known to a person skilled in the art. For example, Hogan et al., Manipulating the Mouse Embryo: A Laboratory Manual, Cold Spring Harbor Laboratory, 1986, or the like can be used as a reference. A technique of introducing foreign DNA into germ cells of mammals was initially developed for mice (Gordon et al., PNAS, 77: 7380-84 (1980); Gordon and Ruddle, Science, 214: 1244-46 (1981); Palmiter and Brinster, Cell, 41: 343-45 (1985); Brinster, et al., PNAS, 82: 4438-42 (1985), etc.). In the present invention also, a gene recombinant non-human mammal can be produced according to these methods.

The gene recombinant non-human mammal of the present invention can be produced, for example, by introducing into a fertilized egg an expression vector into which a mutant SDHC gene derived from mammals has been introduced under the control of a promoter. A method for producing a transgenic non-human mammal which expresses a mutant SDHC gene derived from mammals by introducing the gene will be explained below.

The transgene that is used to produce a transgenic non-human mammal is preferably a recombinant gene obtained by ligating a mutant SDHC gene downstream of a suitable promoter used for mammals. Specifically, the gene described in (1) above in the present specification can be used.

A transgenic non-human mammal, which expresses mutant SDHC by introduction of a mutant SDHC gene, can be produced, for example, by introducing a mutant SDHC gene into a fertilized egg of a non-human mammal, transplanting the fertilized egg into a pseudopregnant female non-human mammal, and then allowing the non-human mammal to give birth to a non-human mammal into which the mutant SDHC gene has been introduced.

Examples of a non-human mammal may include rodents such as a mouse, hamster, Guinea pig, rat, or rabbit, and other animals such as a chicken, dog, cat, goat, sheep, bovine, swine, or monkey. From the viewpoint of simplicity in the production, development and use thereof, rodents such as a mouse, hamster, Guinea pig, rat, or rabbit are preferable. Of these, a mouse is most preferable.

The transgenic non-human mammal used in the present invention is produced by introducing a recombinant gene comprising an foreign mutant SDHC gene into the non-human mammal, or an ancestor thereof, when its germinal cells and germ cells or somatic cells are at the stage of embryogenesis (preferably, at the stage of a single cell or amphicytula, and in general, before the 8-celled embryo stage). The construction of a recombinant gene comprising a mutant SDHC gene is as described above.

Introduction of a mutant SDHC gene at the stage of an amphicytula is carried out such that the mutant gene exists in all the germinal cells and somatic cells of a target mammal. The fact that such a mutant SDHC gene exists in all the germinal cells of an animal produced by introduction of the gene means that the mutant SDHC gene exists in all the germinal cells and somatic cells of progenies of the produced animal. Progenies that inherit the mutant SDHC gene from this type of animal have the gene in all their germinal cells and somatic cells.

After confirming that the transgenic animal of the present invention stably maintains the gene by mating, it can be subjected to serial breeding as an animal containing the gene in an ordinary breeding environment. A homozygous animal, which has the introduced genes in both homologous chromosomes, is obtained. Thereafter, a male homozygous animal is crossed with a female homozygous animal, so that all their progenies can excessively have the mutant SDHC gene. The expression site of the mutant SDHC gene can be identified by observing the expression of the gene at the level of each individual, organ, tissue, and cell. In addition, it is also possible to measure the level of the expression by the enzyme immunoassay using an antibody of the mutant SDHC.

A case where the transgenic non-human animal is a transgenic mouse will be specifically described below. A transgene which comprises cDNA encoding a mutant SDHC gene downstream of a promoter is constructed, and the transgene is then introduced into the male pronucleus of a mouse-fertilized egg by microinjection. The obtained egg is cultured, and it is then transplanted into the oviduct of a pseudopregnant female mouse. Thereafter, the female mouse is bred, and baby mice having the above cDNA are selected from baby mice that are born from the female mouse, so as to produce a transgenic mouse. As a mouse fertilized egg described above, any fertilized egg can be used, as long as it can be obtained by crossing of mice derived from 129/sv, C57BL6, BALB/c, C3H, SJL/Wt, etc.

It is appropriate that the number of the transgene to be injected be between 100 and 3,000 molecules per fertilized egg. Selection of baby mice having the cDNA can be carried out by extracting DNA from the tail of the mice, and subjecting it to the dot hybridization method using the introduced mutant SDHC gene as a probe, the PCR method using specific primers, or the like.

Moreover, as a gene recombinant non-human mammal having the mutant SDHC gene of the present invention, not only the above-described transgenic animal into which the mutant gene has been introduced, but also a hetero non-human mammal obtained by homologous recombination is useful. When a mouse having a mutant SDHC gene is produced, for example, the use of a hetero mouse obtained by homologous recombination is more useful than the production of a transgenic mouse as a means for competing a wild type with a mutant type at a ratio of 1:1. In Examples in the present specification, a transgenic mouse having a mutant SDHC gene was produced. This was intended for representing the induction of mutation and the generation of active oxygen with a on-off switch system, thereby freely controlling the ratio between normal individuals and individuals excessively producing active oxygen.

The gene recombinant non-human mammal of the present invention expresses a mutant SDHC gene, and thereby excessively produces reactive oxygen species (ROS). As a result, the present gene recombinant non-human mammal is preferably characterized in that apoptosis is induced therein at a greater level than that in a wild-type mammal, and that it has a higher tumorigenesis ability than that of a wild-type mammal. Accordingly, the gene recombinant non-human mammal of the present invention is a model that can be used in screening for a substance having action to suppress excessive reactive oxygen species (ROS). In particular, it is useful in screening for an apoptosis inhibitor or anticancer agent.

Furthermore, examples of a portion of the above-described gene recombinant non-human mammal of the present invention may include a cell, a cell organelle, a tissue, and an organ of the non-human mammal, as well as a head, a finger, a hand, a foot, an abdomen, and a tail thereof. All these parts are also included in the scope of the present invention.

(3) Screening for Substance Having Action to Suppress Excessive Reactive Oxygen Species (ROS)

The method of the present invention for screening for a substance having action to suppress excessive reactive oxygen species (ROS) can be carried out using the gene recombinant non-human mammal of the present invention that expresses mutant SDHC. This is to say, a test substance is administered to the gene recombinant non-human mammal of the present invention (for example, a transgenic mouse, etc.), and the physiological data of the transgenic non-human mammal is evaluated or studied, so that the action of the test substance to suppress reactive oxygen species (ROS) can be evaluated. Such a substance having action to suppress excessive reactive oxygen species (ROS) can be a candidate substance for an apoptosis inhibitor or anticancer agent.

Examples of a test substance used for the screening method of the present invention may include nucleic acid (for example, DNA, RNA, or antisense RNA), a carbohydrate, a lipid, a protein, an antibody, a peptide, a peptide-like form, a low molecular weight synthetic compound, a fermented product, a cell extract, a plant extract, an animal tissue extract, and a blood plasma. Such a test substance may be either a novel substance or a known substance. In addition, a library containing a large number of molecules, such as a peptide library or compound library, may also be used as a test substance.

Examples of a method of administering a test substance to the gene recombinant non-human mammal of the present invention may include oral administration and intravenous injection. The dosage of a test substance can be selected as appropriate, depending on an administration method, the characteristics of a test substance, or other factors.

The present invention will be further specifically described in the following examples. However, these examples are not intended to limit the scope of the present invention.

EXAMPLES

Example 1

(A) Experimental Procedures (1) Predicted Amino Acid Sequences of SDHC Gene

The amino acids sequences of *E. coli* (accession number: AE005250), *C. elegans* (L26545-1), *Mus musculus* (AK032458-1), *Bos taurus* (S74803-1) and *Homo sapiens* (D49737-1) and the sequences of complete cDNA's (cds) of *E. coli* (accession number: AE000175 or U00096), *C. elegans* (NM_066882), *Mus musculus* (NM_025321), *Bos taurus* (NM_175814) and *Homo sapiens* (NM_003001) named SDHC, cyt-1 or cytochrome b large subunit were retrieved from DDBJ/GenBank/EMBL and Entrez Nucleotide of National Center for Biotechnology Information (NCBI), respectively.

(2) Mouse SDHC cDNA Cloning

The DNA sequence of SDHC, a mouse homologue of *C. elegans* cyt-1 gene was obtained from DDBJ (http://www.ddbj.nig.ac.jp/E-mail/homology.html). Wild-type SDHC PCR products were obtained from the templates of liver cDNA in an ICR mouse strain (primers: 5'-GGG GAA TTC ATG GCT TTC TTG CTG AGA CAT GTC AGC (SEQ ID NO: 3) and 3'-GGG AAG CTT TCA CAG GGC GGC CAG CCC) (SEQ ID NO: 4) and then were inserted in a pBluescript II SK-vector at EcoRI-HindiIII site.

(3) Construction of A mev-1 mutant-type SDHC Gene and Establishment of The Mutant Cell Lines The mutant allele was proliferated by PCR amplification (primers: 5'-GGG GAA TTC CTC TTC CCA TGG CAC TGT CCG AAT GCC (SEQ ID NO: 5) and 3'-GGG AAG CTT TCA CAG GGC GGC CAG CCC (SEQ ID NO: 6)). This 5' primer contains the substituted nucleotide, and the PCR products were substituted at an Earl-HindIII cutting site in the pBluescript II SK-vector including the wild-type SDHC gene. This fragment was inserted in an expression vector containing basal transcription region of cytomegalovirus promoter (PminCMV), and the vector DNA was integrated in the chromosome of mouse embryonic fibroblast culture cells (NIH3T3 cells) by using the Ripofectamin-plus transfection reagent (Invitrogen Inc.).

(4) Cell Culture

The cells were cultivated in DMEM medium (Nissui Company) including 2.5% FBS+2.5% CS in a 5% $CO_2$ incubator. Cell division and proliferation were examined after synchronous culture in GO phase into exhaustion of serum medium and at the contact inhibition state. The cell culture method in soft-agar medium employed DMEM medium including 2.5% FBS+2.5% CS containing 0.33% soft-agar (Difco Noble Agar) on the same medium contained 0.5% soft-agar. Cells were grown in a 5% $CO_2$ incubator.

(5) CoQ Treatment

There are different species-specific isoforms of CoQ that vary in the number of isoprene side-chain units. For example, $CoQ_8$, $CoQ_9$ and $CoQ_{10}$ predominate in *Eschericia coli, C. elegans* and humans, respectively. In the experiments described above, a final concentration of 2 μg/ml $CoQ_{10}$, which is considered to be the most effective isoform, was used (Ishii, N., et al., (2004), Mech. Ageing Dev. 125, 41-46).

(6) $O_2^-$ Measurement $O_2^-$ production was measured using the chemiluminescent probe MPEC (2-methyl-6-p-methoxyphenylethynyl-imidazopyrazinone) (ATTO Company), which is modified from a MCLA method as described by Senoo-Matsuda, et al., (2001) J. Biol. Chem. 276, 41553-41558. 40 μg of intact mitochondria was added to 1 ml of assay buffer (50 mM HEPES-NaOH, pH 7.4, 2 mM EDTA) containing 0.7 μM MPEC. For the measurement of $O_2^-$ production from mitochondria with substrate and inhibitor, 1.5 mM succinate as a complex II substrate was added to the mitochondrial solution, and 2 μg/ml of QNO (2-heptyl-4-hydroxy-quinoline-N-oxide) as a complex III inhibitor was added after addition of the mitochondria and succinate. These solutions were placed into the photon counter with an AB-2200 type Luminescencer-PSN (ATTO Company) and measured at 37° C. The rates of $O_2^-$ were expressed as counts per second, and the amounts were calculated by subtracting the optical density of samples in the presence of 10 μg/ml bovine Cu, Zn-superoxide dismutase from that in the absence of the enzyme.

(7) The Procedure for Slot-blot Analysis of Protein Carbonyls Measurement

Protein carbonyl accumulation was measured by using the anti-DNPH (2,4-Dinitrophenyl hydrazine) antibodies. 0.5 ml of lysis buffer (10 mM Tris-HCl, 100 mM NaCl, 0.1% NP-40, 1 mM EDTA, 0.1 mM p-APMSF) was added in culture cells in a 10 cm dish, and protein carbonyls contents of the extracts were determined by the DNPH method as described by Levine, R. L. et al., (1990) Methods Enzymol. 186, 464-478. The protein carbonyls contents of the DNPH-treated cell extractions were measured by slot-blot analysis using MilliBlot-S (Millipore Company). The extractions were transferred to nitrocellulose membranes (Amersham Pharmacia Biotech Company), and the membranes were treated with anti-DNPH antibodies in TEN buffer (10 mM Tris-HCl, 1 mM EDTA, 100 mM NaCl) containing 5% skim milk. After washing with the buffer without the antibodies, the membranes were treated with an ECL-plus western blotting detection system (Amersham Biosciences) after treated anti-rabbit antibodies and were exposed to Hyperfilm™ ECL chemiluminescence film (Amersham Biosciences) at room temperature for 2 minutes. The chemiluminescence's signals were visualized in a CS Analyzer and AE-6962 light capture (ATTO Company).

(B) Results (1) Identification of SDHC and Establishment SDHC E69 Cell Lines

Figure 1C:
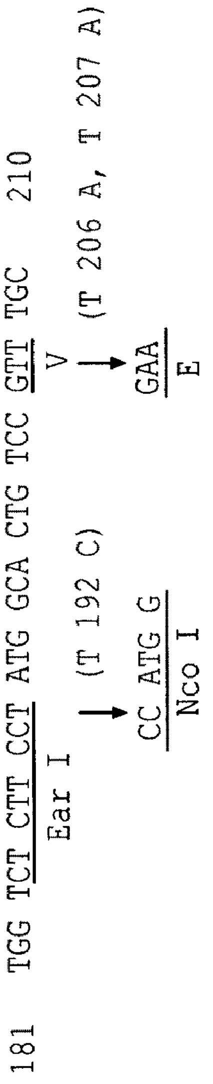
Figure 1D:
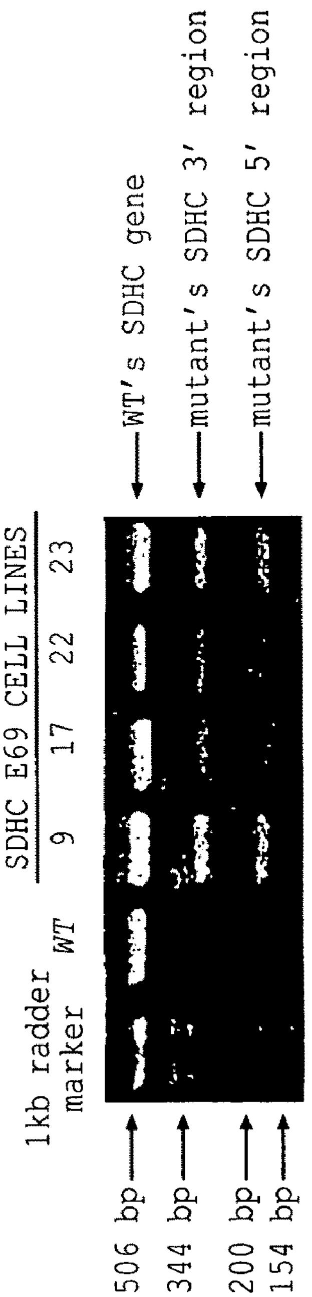

The SDHC subunit of succinate-coenzyme Q (CoQ) [also known as ubiquinone or 2,3-dimethoxy-5-methyl-6-multiprenyl-1,4-benzoquinone] oxidoreductase possesses both the active site as well as the binding site to Heme and CoQ. The amino acid sequence at this region is highly conserved among animals (FIG. 1A) (Yu, L. et al., (1992) J. Biol. Chem. 267, 24508-24515; Hagerhall, C. et al., (1996) FEBS Lett. 389, 25-31; Yang, X. et al., (1998) J. Biol. Chem. 273, 31916-31923; Vibat, C. R., (1998) Biochemistry 37, 4148-4159; Scheffler, I. E. (1998) Prog. Nucleic. Acid. Res. Mol. Biol. 60, 267-315; Ackrell, B. A. (2000) FEBS Lett. 466, 1-5; and Yankovskaya, V. et al., (2003) Science 299, 700-704). To construct a mutant SDHC transgene, the mouse SDHC gene was modified to convert a valine to glutamic acid at position 69 (SDHC Val69Glu). This corresponds to the amino acid substitution of glutamic acid from glycine at position 71 (Gly71Glu) in the *C. elegans* mev-1 mutant allele kn1 (FIGS. 1, B and C). This gene was transfected in mouse fibroblast NIH3T3 cells. From the transfected cells, cell lines that expressed equal amounts of mRNA from the transgenic and wild-type alleles were selected. They were named SDHC E69 cell lines (FIG. 1D). Full knockout cell lines were not obtained, most likely because evidence indicates that cells with more than 80% abnormal mitochondrial DNA are inviable (Nakada, K. et al., (2001) Biochem. Biophys. Res. Commun. 288, 901-907).

(2) SDHC E69 Cell Lines Overproduce $O_2^-$ from Mitochondria

Figure 2A:
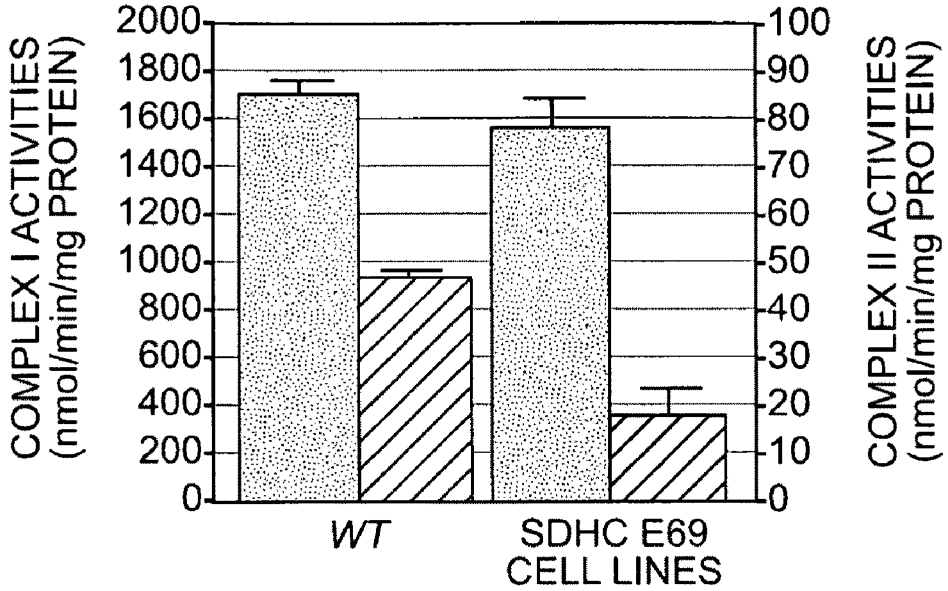
Figure 2B:
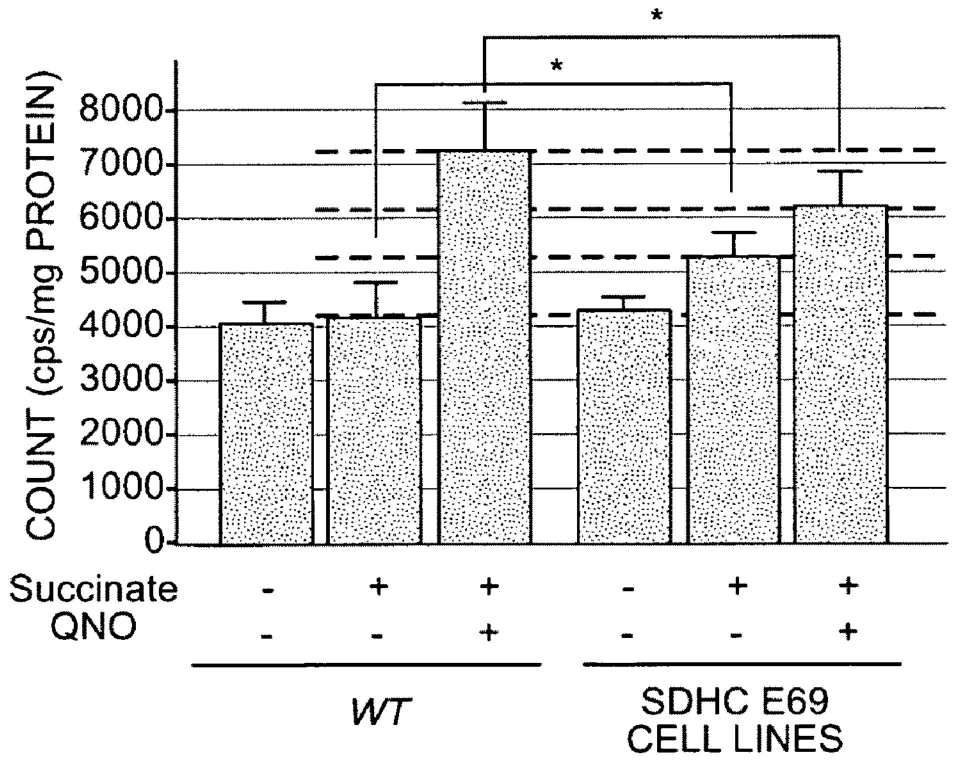

It has been previously established that the mev-1 of *C. elegans*, which is the nematode equivalent to SDHC E69, is oxygen-hypersensitive because of the overproduction of $O_2^-$ from mitochondria caused by the reduction of complex II activity (Senoo-Matsuda, et al., (2001) J. Biol. Chem. 276, 41553-41558). To test whether or not the mouse SDHC E69 cell line suffers from mitochondrially produced oxidative stress, it was first determined that the enzymatic activity of complex II (succinate-CoQ oxidoreductase) was reduced by 30% relative to wild type, whereas the activity of complex I (NADH-CoQ oxidoreductase) in SDHC E69 cells was identical to that of wild type (FIG. 2A). Second, $O_2^-$ production from the mutant mitochondria was examined. In wild-type cells, there was no difference in $O_2^-$ production when succinate was added as a substrate of complex II. Conversely, the level increased when a Complex III inhibitor QNO (2-heptyl-4-hydroxy-quinoline N-oxide) was added to induce electron leak from complex III (FIG. 2B). This is consistent with the notion that $O_2^-$ is normally produced at complex III of the electron transport system. Unlike with the wild-type cells, the $O_2^-$ level in the SDHC E69 cells increased even when succinate was added (FIG. 2B). This is not a generalized feature of this cell line, because levels were somewhat lower than wild type when the inhibitor for complex III was added. The $O_2^-$ levels of both wild-type and SDHC E69 cells were not affected when NADH was added as a substrate of complex I. In concert, these data suggest that, as with mev-1 in *C. elegans*, elevated $O_2^-$ is generated at complex II in SDHC E69 cells.

Figure 2C:
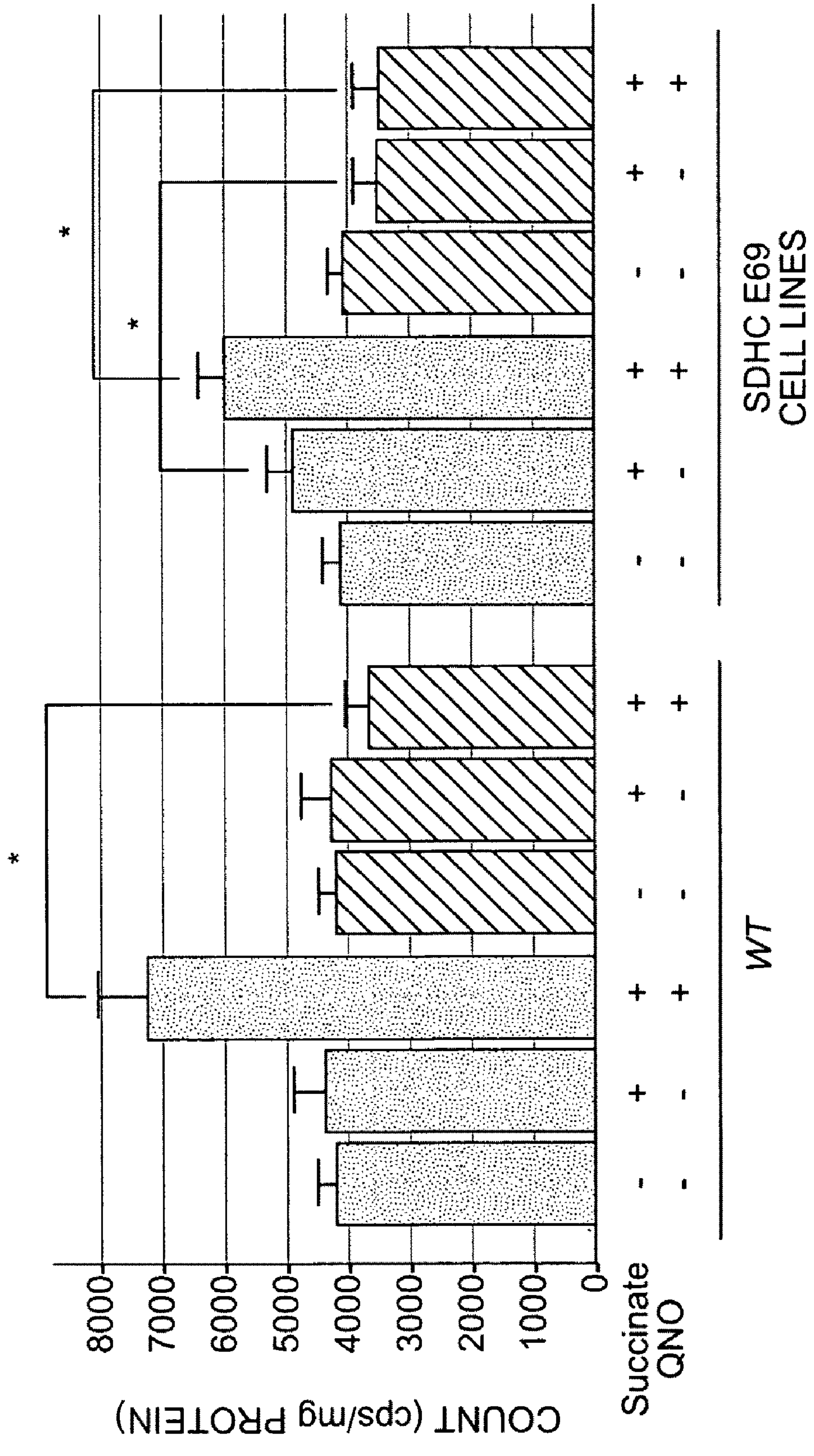
Figure 2D:
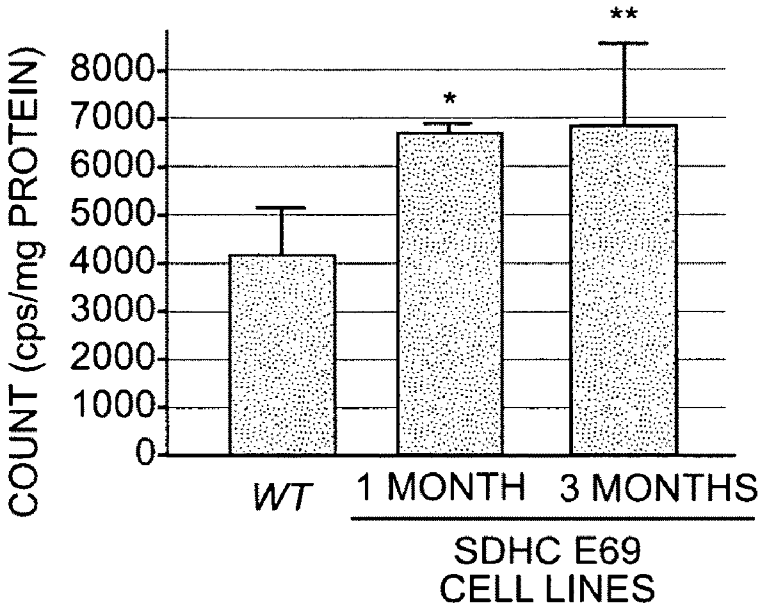

The mutation in SDHC gene of the SDHC E69 cells may lead to loss of CoQ binding because it is known that this is an important region for binding between complex II and CoQ (Yang, X. et al., (1998) J. Biol. Chem. 273, 31916-31923; Ackrell, B. A. (2000) FEBS Lett. 466, 1-5; and Yankovskaya, V. et al., (2003) Science 299, 700-704). Therefore, the effects of exogenously added CoQ on SDHC E69 cells were measured. It has been demonstrated previously that addition of the CoQ 10 isoform reduced $O_2^-$ levels in mev-1 mutant of *C. elegans* (Ishii, N., et al., (2004), Mech. Ageing Dev. 125, 41-46). This proved to be the case with SDHC E69, as $O_2^-$ levels were significantly suppressed by CoQ addition (FIG. 2C). Collectively these data support the notion that SDHC E69 cells overproduce $O_2^-$ owing to electron leakage from complex II, and that altered CoQ binding is responsible for this effect. These in vitro data are consistent with observations made on superoxide anion levels in intact cells. Specifically, $O_2^-$ levels were significantly higher in intact mitochondrial isolated from SDHC E69 cells one month and three months after establishment (FIG. 2D).

(3) Mitochondrial $O_2^-$ Results in Damage to Intracellular Components

Figure 3A:
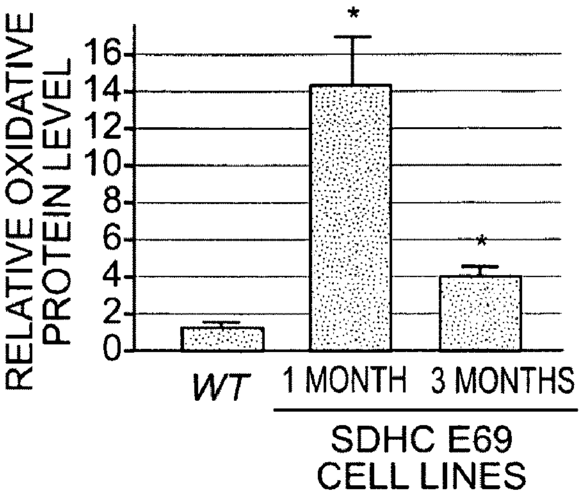
Figure 3B:
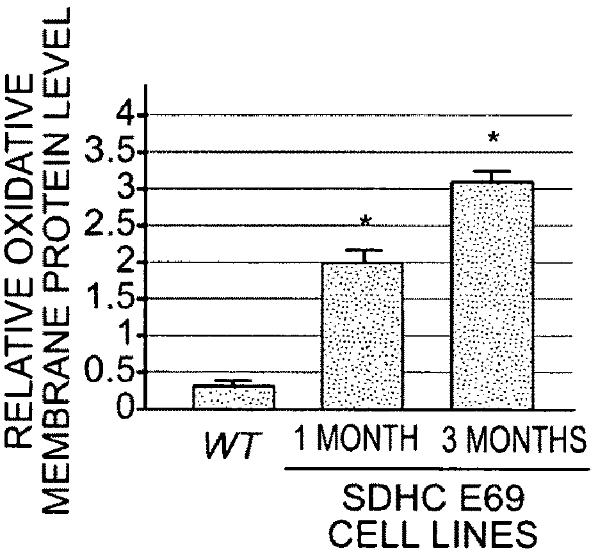
Figure 3C:
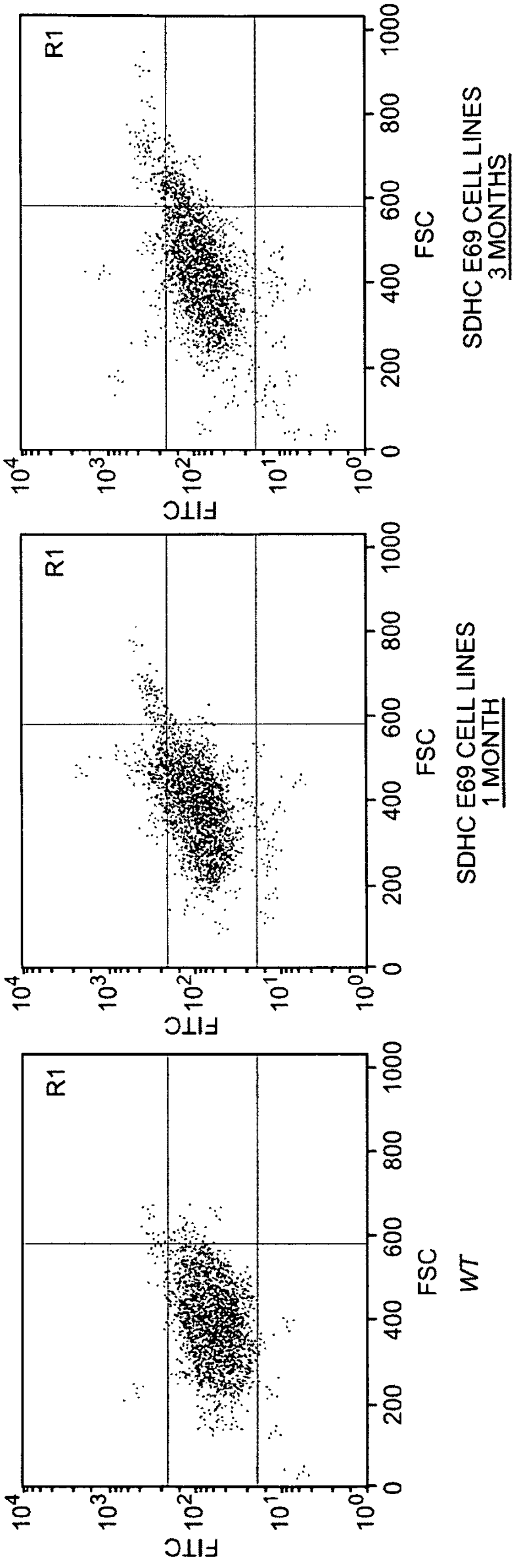
Figure 3D:
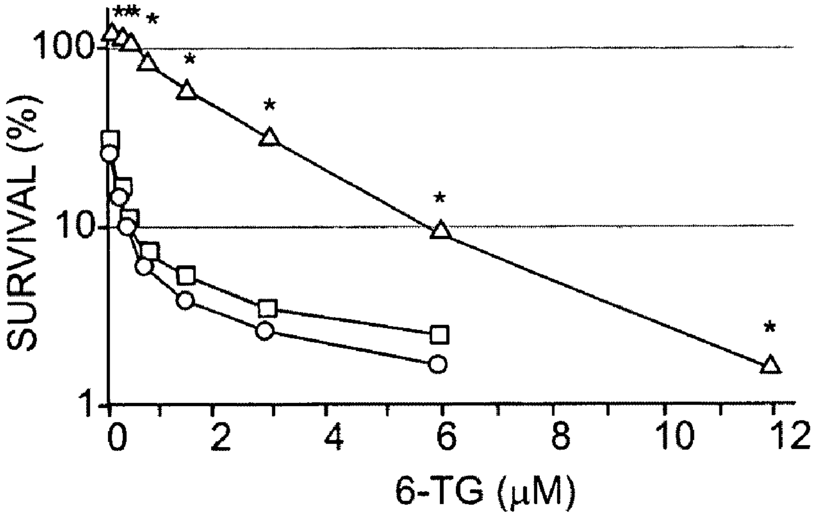
Figure 3E:
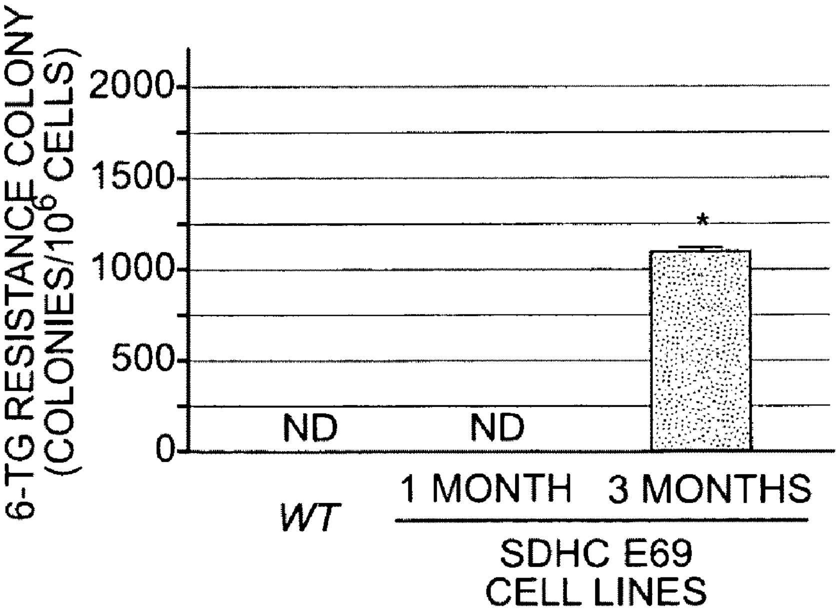

It is known that oxidative stress can damage cellar components such as proteins (Stadtman, E. R. (2001) Ann. N Y Acad. Sci. 928, 22-38) and DNA (Toyokuni, S. (1999) Pathol. Int. 49, 91-102; Cooke, M. S. et al., (2003) FASEB J. 17, 1195-1214; and Marnett, L. J. (2000) Carcinogenesis, 21, 361-370). The one-month SDHC E69 cells accumulated cytoplasmic carbonyl proteins, a marker of oxidative stress, at a faster rate than wild type (FIG. 3A). Accumulation was slower in the three-month cells but was still significantly higher than in the wild-type cells (FIG. 3A). The carbonyl proteins in membrane fractions increased with increasing passage time in the SDHC E69 cells and were again significantly higher than in wild type (FIG. 3B). In addition, the amount of 8-OH-deoxyguanine (8-OHdG), a DNA marker of oxidative stress (Kasai, H. (1997) Mutat. Res. 387, 147-163) was two-fold higher in SDHC E69 cells (FIG. 3C). Given that 8-OhdG is a major premutagenic lesion, the resistance to 6-thioguanine (6-TG) was examined as an indicator of mutations in the hypoxanthine phosphoribosyl transferase (hprt) gene (Knaap, A. G. et al., (1975) Mutat. Res. 30, 97-110; and Tsutsui, T. et al., (1981) Mutat. Res. 80, 357-371). The three-month SDHC E69 cells were approximately two times more resistant than the one-month SDHC E69 and wild-type cells (FIG. 3D). In addition, only three-month SDHC E69 cells displayed colony forming ability under a 6-TG concentration that allowed 2% survival under short-term culturing conditions (FIG. 3E). Most importantly, these data demonstrate that SDHC E69 cells were hypermutable.

Figure 4A:
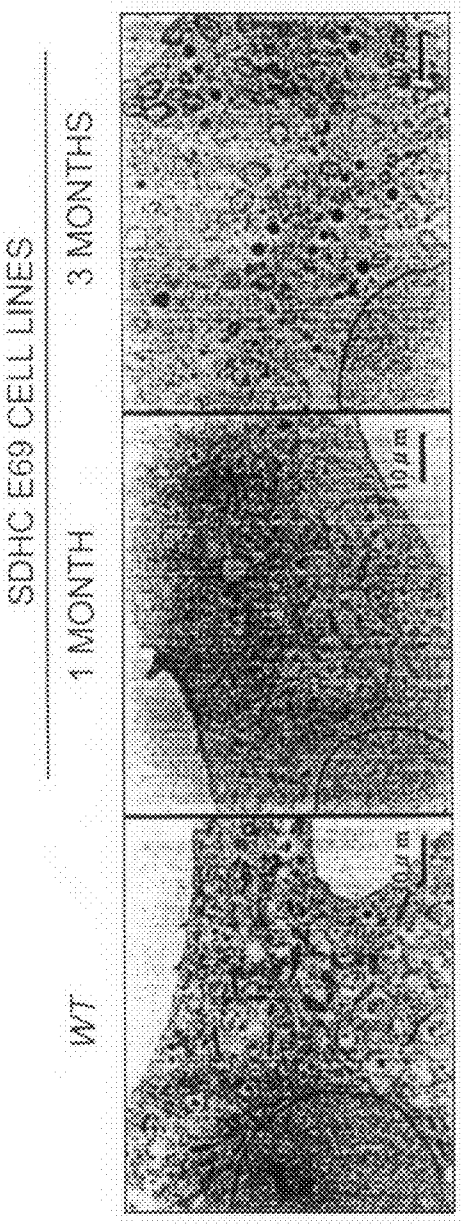
Figure 4B:
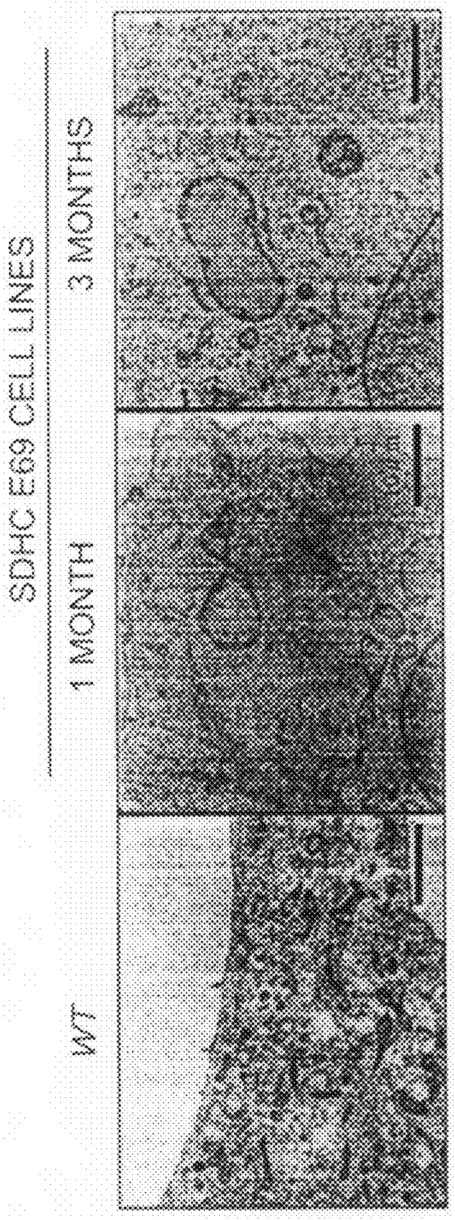
Figure 4C:
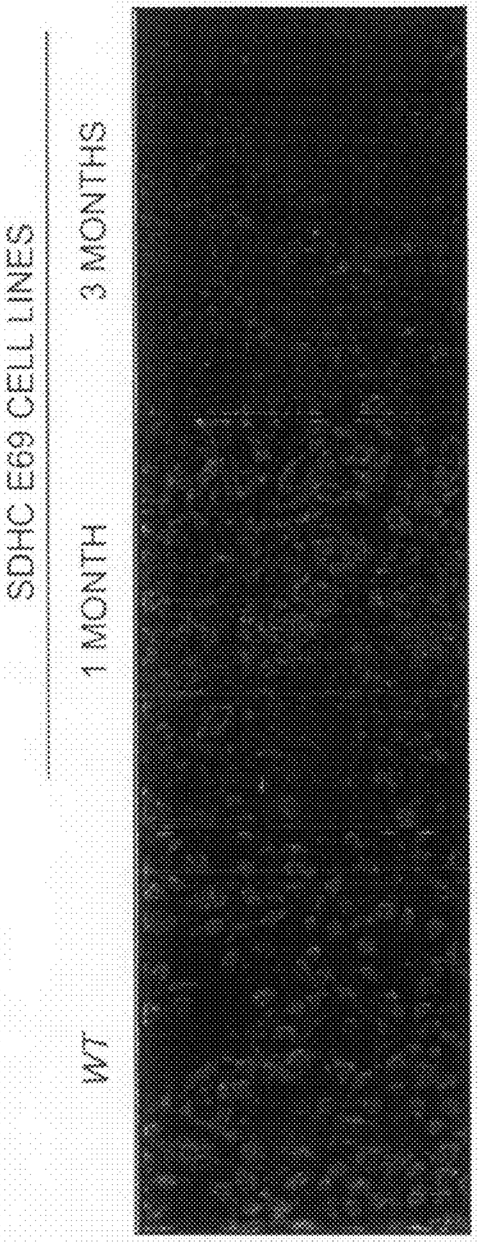
Figure 4D:
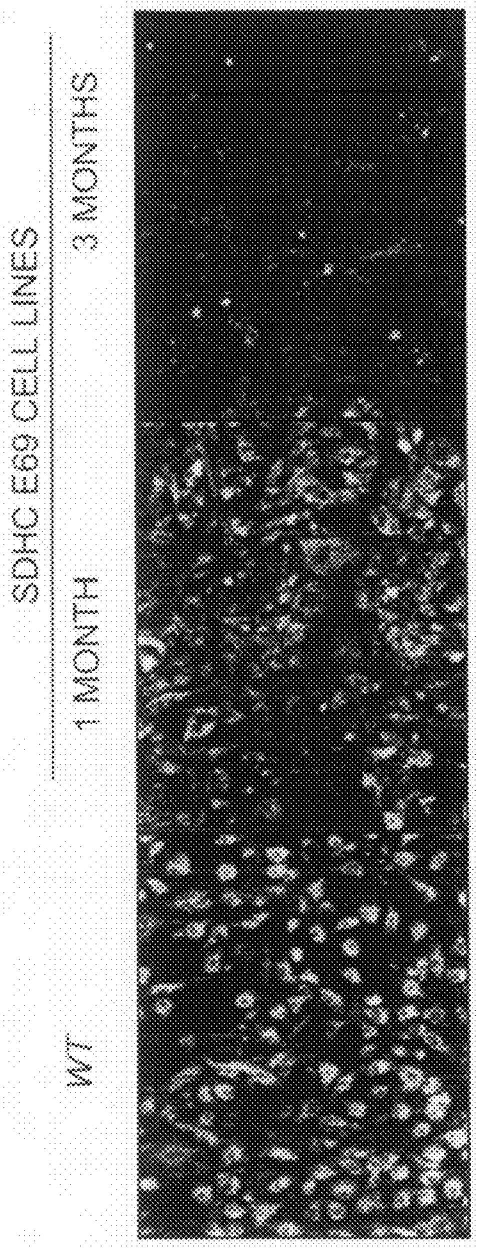

(4) Alteration of Mitochondrial Structure and Membrane Potential in SDHC E69 Cell Lines Electron micrographs revealed that the distribution of mitochondria in wild-type and SDHC E69 cells was the same, with most mitochondrial located around nuclei in both strains (FIG. 4A). However, many mitochondria in SDHC E69 cells had disorganized cristae. In addition, many mitochondria were swollen and enlarged (FIGS. 4, A and B). The enlargement might have resulted from mitochondrial fusion to compensate dysfunctional mitochondria (Griparic, L. et al., (2001) Traffic. 2, 235-244; Westermann, B. (2002) EMBO Rep. 3, 527-531; and Mozdy, A. D. et al., (2003) Natl. Rev. Mol. Cell. Biol. 4, 468-478). In addition, the lipophilic cation JC-1 was employed to determine the level of phospholipids and membrane potential in SDHC E69 and wild-type cells. Excitation at 485±11 nm provided an indication of phospholipid levels while excitation at 535±17.5 nm allowed determination of relative membrane potential. SDHC E69 cells contained reduced amounts of phospholipids in the mitochondrial membrane (FIG. 4C). In addition, membrane potential was significantly less in SDHC E69 than in wild type (FIG. 4D).

(5) Characterization of SDHC E69 Cell Lines

Figure 5A:
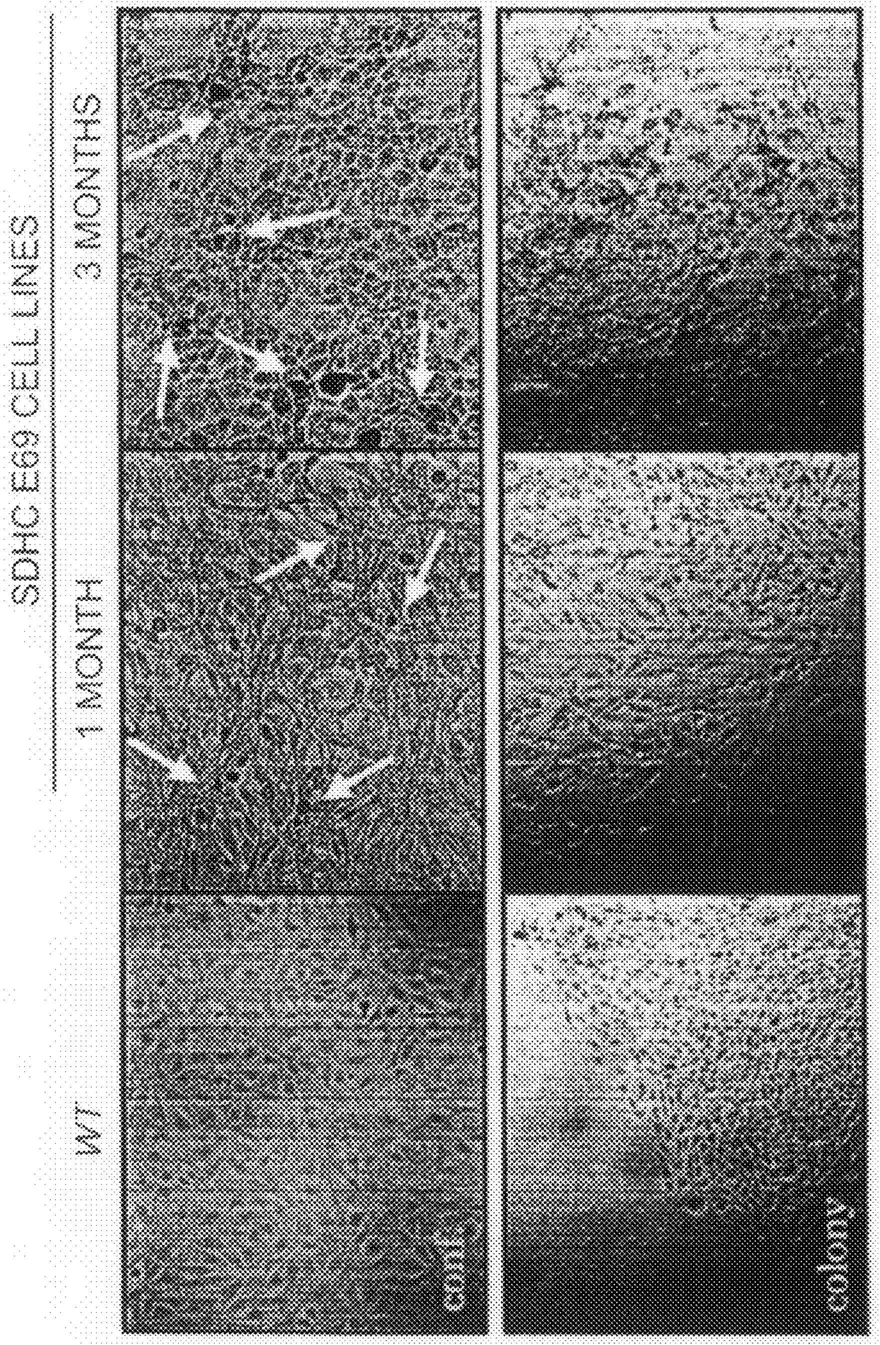
Figure 5B:
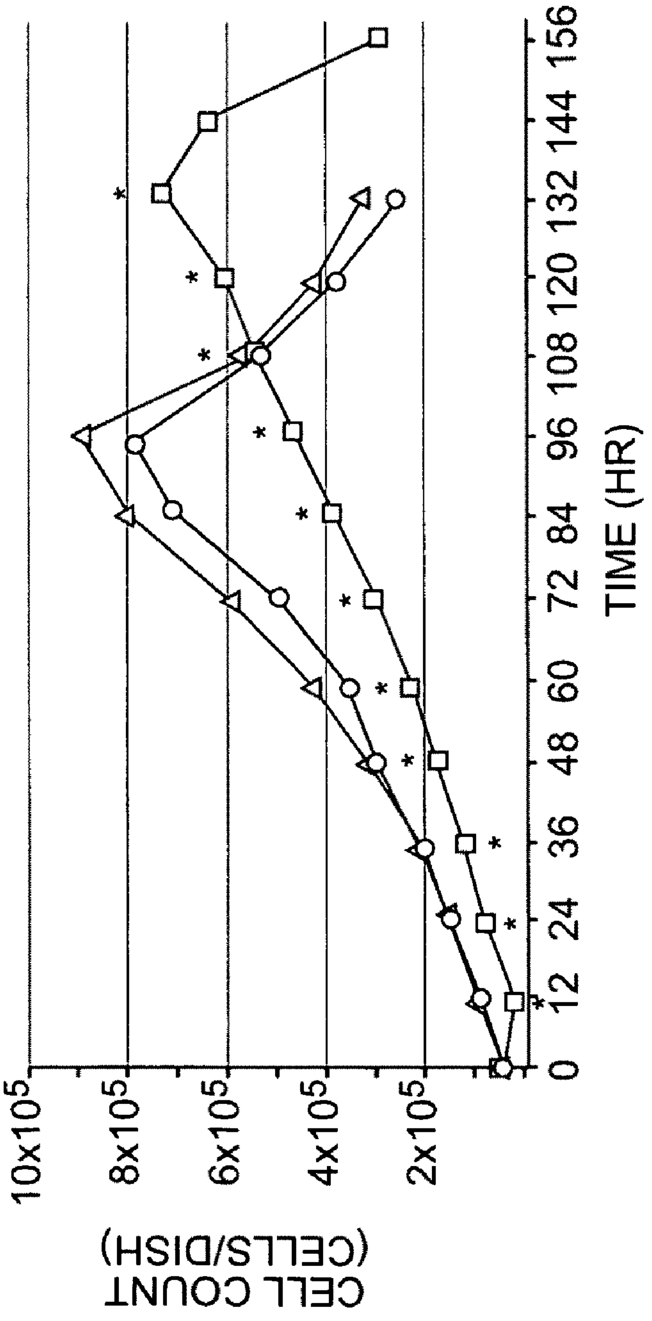

During three months (the period of colony formation on medium plates), wild-type NIH3T3 cells maintained normal fibroblast morphology and grew in a monolayer. Conversely, the SDHC E69 cells showed loss of contact inhibition and had many apoptotic molecule-like granules during the first month after establishment. During the period of colony formation, some clefts which are characteristic of programmed cell death, were found in the center of some colonies (FIG. 5A) (Kroemer, G. et al., (1998) Annu. Rev. Physiol. 60, 619-642; and Zimmermann, K. C. et al., (2001) Pharmacol. Ther. 92, 57-70). In three-month SDHC E69 cells, the morphology was changed from the flattened and elongated morphology typical of fibroblasts to that of smooth and rounded cells. The same changes were evident, although to a lesser degree in the one-month SDHC E69 cells. In addition, the SDHC E69 cells formed multiple layers (FIG. 5A). The doubling time of one-month SDHC E69 cells was 1.5 to 2 times slower than that of wild-type cells (36 to 48 hr for one-month SDHC E69 cells versus 20 to 24 hr for wild-type cells). However, the doubling time in three-month SDHC E69 cells was completely recovered to that of wild type (FIG. 5B). The recovery to normal growth rates in the three-month SDHC E69 cells may have been the consequence of physiological adaptations. Alternatively, it may be related to the transformation process. Inclusion of $CoQ_{10}$ in the growth medium also resulted in normal doubling times in the SDHC E69 cells, indicating that oxidative stress was responsible for the longer generation times in the transgenic cell line.

(6) Abnormal SDHC E96 Mitochondria Cause Apoptosis

Figure 6B:
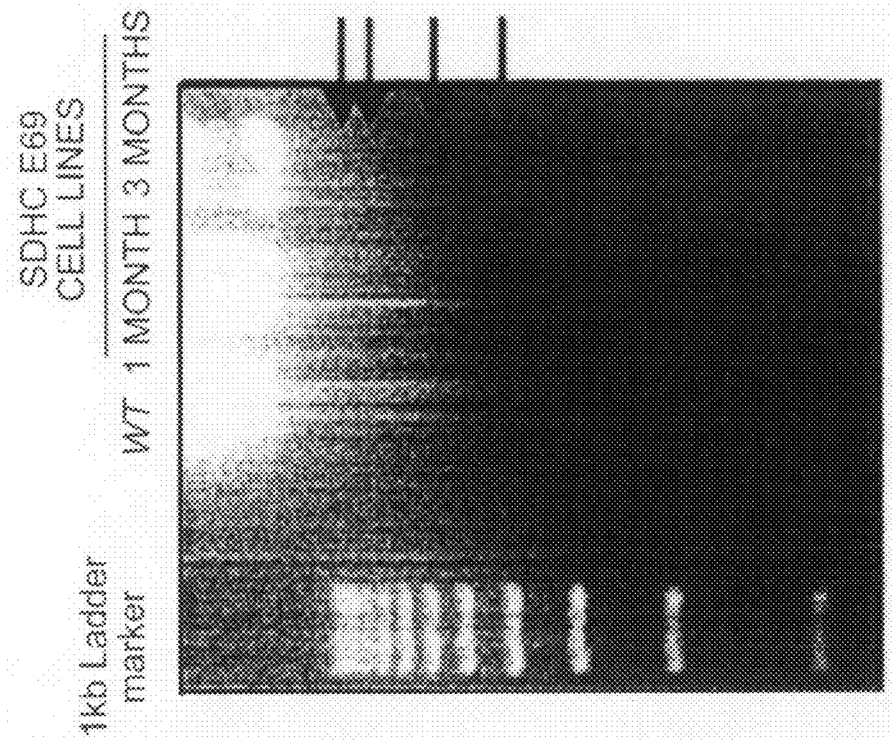
Figure 6A:
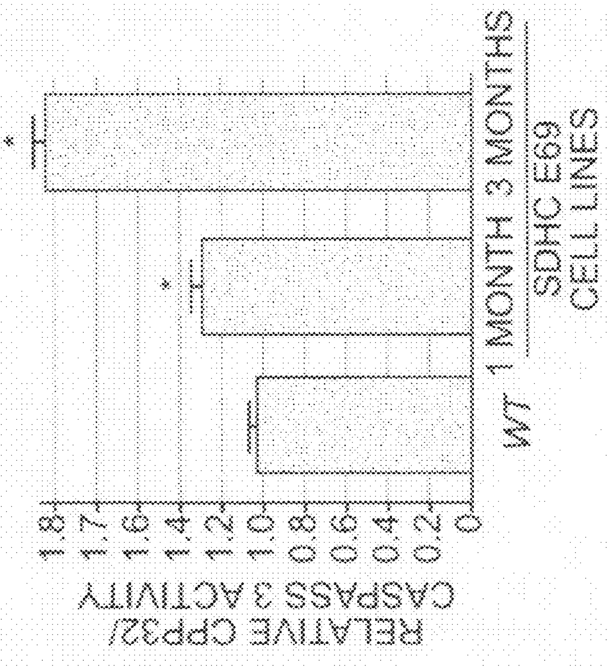

There are many reports that excess ROS cause apoptosis or cancer. For example, it was found that the mev-1 mutant of *C. elegans*, which is the nematode equivalent to SDHC E69, is oxygen hypersensitive and contains supernumerary apoptotic cells because of overproduction of $O_2^-$ from mitochondria. This suggested that apoptosis is also probably caused by the oxidative stress from mitochondria in mouse SDHC E69 cells. It is known that morphological abnormalities are often indicative of reduced membrane potential and can lead to the activation of caspases (Kroemer, G. et al., (1998) Annu. Rev. Physiol. 60, 619-642; Degan, W. G. et al., (2000) Cell. Death. Differ. 7, 616-627; and Robertson, J. D. et al., (2000) J. Struct. Biol. 129, 346-358). In turn, caspase activation results in a series of events, including degradation of nuclear DNA into nucleosome-length fragments, that culminates in apoptosis (Wakabayashi, T. (1999) Acta. Biochim. Pol. 46, 223-237; Degan, W. G. et al., (2000) Cell. Death. Differ. 7, 616-627; and Robertson, J. D. et al., (2000) J. Struct. Biol. 129, 346-358). SDHC E69 cells were examined for these pathologies. First, the activity of the apoptosis marker caspase 3 (Zimmermann, K. C. et al., (2001) Pharmacol. Ther. 92, 57-70; Thress, K. et al., (1999) J. Bioenerg. Biomembr. 31, 321-326; Budihardjo, I. et al., (1999) Annu. Rev. Cell. Dev. Biol. 15, 269-290; and Porter, A. G. et al., (1999) Cell. Death. Differ. 6, 99-104) was 1.3 to 1.8 times higher in SDHC E69 cells (FIG. 6A). Second, DNA fragmentation was detectible in three-month SDHC E69 but not wild-type cells (FIG. 6B). Neither of these was observed in the one-month SDHC E69 cells, perhaps because the intracellular stress was lower at one month. The intracellular stress appears to be lower than that produced by strong oxidants such as paraquat. In contrast, these data indicate that phenotypes such as growth delay, lost of cellular contact inhibition, appearance of apoptotic molecule-like granules and morphological abnormality of mitochondrial structures are consistent with intracellular oxidative stress that leads to apoptosis.

(7) Transformation is Elevated in SDHC E69 Cells

Figure 6C:
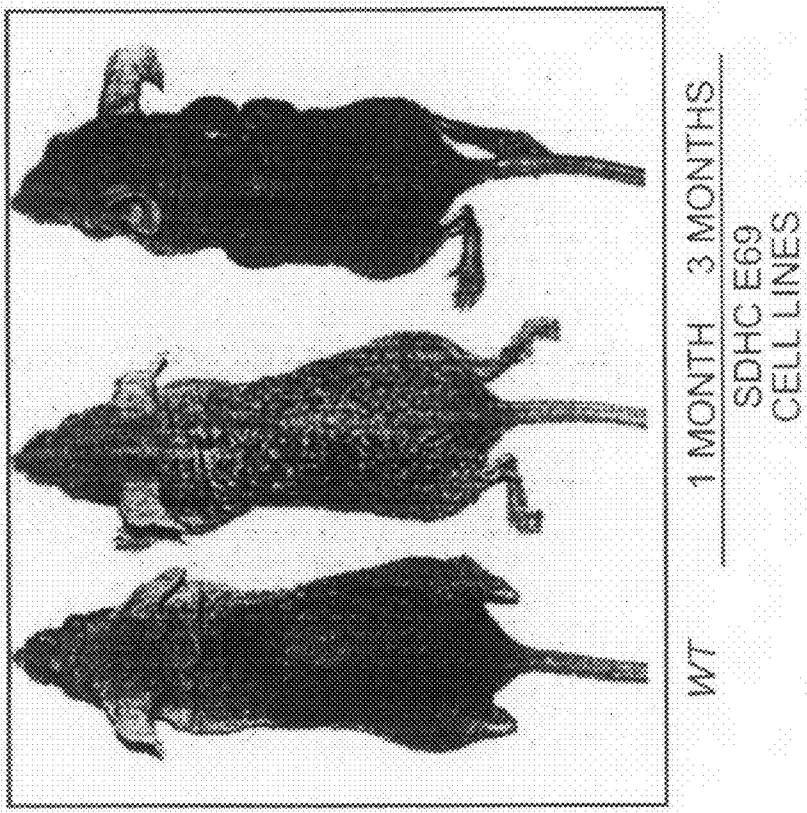

When injected under the epithelium of nude mice, one-month SDHC E69 cells rapidly disappeared as compared to those of wild type. This suggests that these cells were dying by apoptosis and were phagocytized shortly after injection. Conversely, injection of the same number of three-month SDHC E69 cells resulted in the production of tumors within two weeks (FIG. 6C).

Figure 6D:
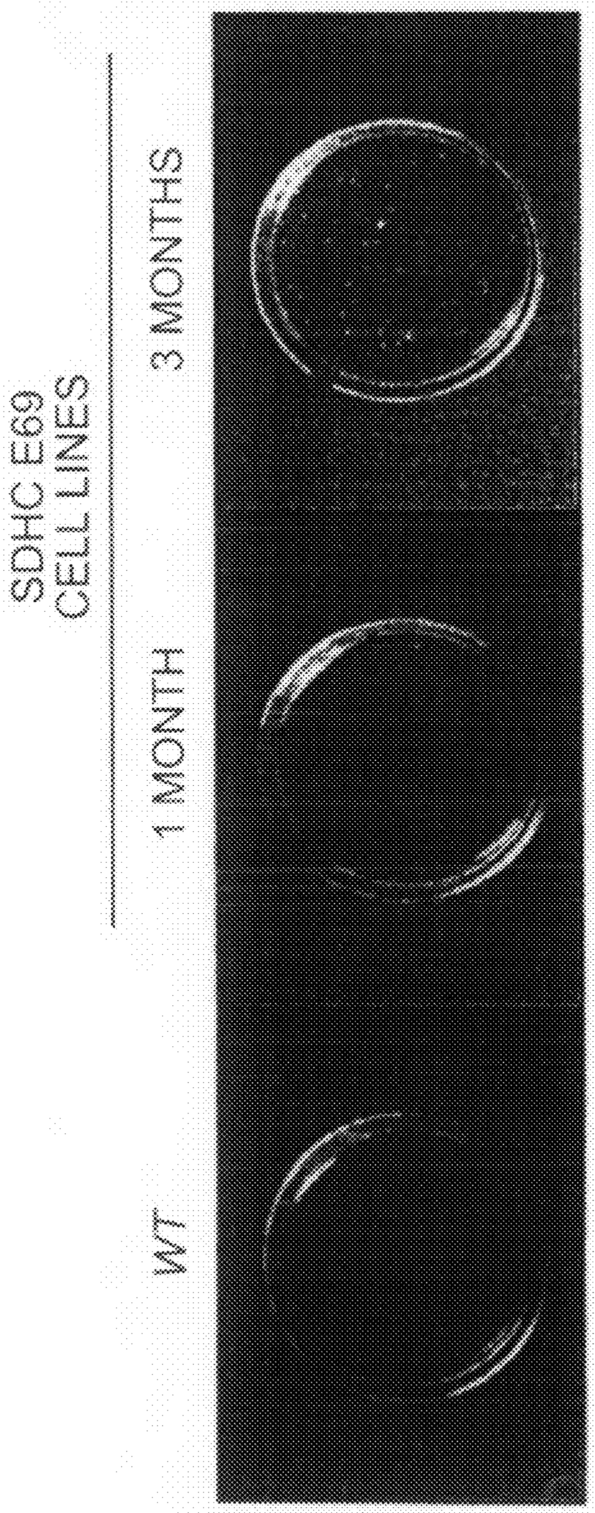

It is known that neoplastic transformation is the consequence of multiple mutations to oncogenes and tumor suppressor genes (Toyokuni, S. (1999) Pathol. Int. 49, 91-102; Cooke, M. S. et al., (2003) FASEB J. 17, 1195-1214; Olinski, R. et al., (1998) Acta. Biochim. Pol. 45, 561-572; and Kang, D. H. (2002) AACN Clin. Issues. 13, 540-549). Only the three-month SDHC E69 cells displayed colony forming ability under a 6-TG concentration that allowed 2% survival under short-term culturing conditions (FIG. 3E). Most importantly, these data demonstrate that SDHC E69 cells were hypermutable. In addition, since tumor cells generally acquire anchorage-independent growth (Colbum, N. H. et al., (1978) Cancer Res. 38, 624-634; and Suh, Y. A. et al., (1999) Nature 401, 79-82), a soft-agar culture method was employed to access this property in SDHC E69 cells. The three-month SDHC E69 cells made many colonies in this medium (FIG. 6D). The transformation rates during one month were $5\times10^{-4}$ cells for the one-month SDHC E69 cells and $5\times10^{-3}$ for the three-month cells, respectively. Conversely, the transformation rate of NIH3T3 cells was less than $1\times10^{-6}$. Thus, the SDHC E69 cells had 100- to 1,000-fold higher transformation rates than wild-type cells (Table I).

TABLE 1

Transformation rates of NIH3T3 wild-type and SDHC E69 cells on soft-agar medium

| Cell | After 2 weeks (colony/$10^4$ cells) | After 1.5 month (colony/$10^4$ cells) | Transformation rate during 1 month $1\times10^4$ cells |
|---|---|---|---|
| Wild type | no detection | no detection | no detection |
| | SDHC E69 cells | | |
| 1 month | 1.04 ± 1.80 | 6.25 ± 3.13 | 5.21 ± 1.8 |
| 3 months | 506 ± 23 | 552 ± 19 | 45.5 ± 4.6 |

Example 2

Production of Transgenic Mouse Having mev-1 Mutant SDHC Gene (A) Production of Transgene of mev-1 Conditional Transgenic mice (1) Amplification and Isolation of DNA Fragment of Cytomegalovirus Promoter (PhCMV Promoter) by PCR Method Novel restriction enzyme recognition sites were inserted into both ends of a PhCMV promoter by the PCR method (this is referred to as Gene 1). A pcDNA3 plasmid vector containing a PhCMV promoter was used as a template in the PCR. Primers used in the PCR were 5' primer oligo nucleotide: ggg ggt acc aat att gct agc gag ctt ggc cca ttg cat acg ttg (SEQ ID NO: 7) and 3' primer oligo nucleotide: ggg ctc gag cac gtg aag ctt cgg atc cga att cgc tag cgg ggc cgc gga ggc tgg atc (SEQ ID NO: 8).

The pcDNA3 plasmid vector was subjected to a treatment with a restriction enzyme HindIII and a blunt end treatment, so as to eliminate a HindIII restriction enzyme recognition site (the obtained vector is referred to as Vector 1).

Vector 1 was treated with restriction enzymes KpnI-XhoI. Thereafter, Gene 1, which had been treated in the same manner as above, was inserted into the vector, so as to produce Vector 2.

(2) Addition of Polyadenylate Signal (Poly A)

SV40 poly A that had been treated with restriction enzymes BamHI-HindIII was inserted into a plasmid vector Vector 2 treated in the same manner as above, so as to produce Vector 3.

(3) Addition of Tetracycline-Dependent Transcriptional Activator (rTetR-VP16)

A pUHD17 plasmid vector (Clontech) was treated with restriction enzymes BamHI-EcoRI to obtain a transcriptional activator rTetR-VP16. The transcriptional activator rTetR-VP16 was then inserted into a plasmid vector Vector 3 treated by the same restriction enzyme treatment, so as to produce Vector 4.

(4) Amplification and Isolation of DNA Fragment of SV40 Poly A by PCR Method

Novel restriction enzyme recognition sites were inserted into both ends of SV40 poly A by the PCR method (this is referred to as Gene 2). A pcDNA3 or pTRE plasmid vector containing SV40 poly A was used as a template in the PCR Primers used in the PCR were 5' primer oligo nucleotide: ggg gga tcc aga cat gat aag (SEQ ID NO: 9) and 3' primer oligo nucleotide: ggg ggt acc ggg ccc aga tct ggt cga gct gat act tcc (SEQ ID NO: 10). The pcDNA3 plasmid vector was treated with restriction enzymes BamHI-KpnI. Then, Gene 2 treated in the same manner as above was inserted into the above plasmid vector, so as to produce Vector 5.

(5) Production of Tetracycline-dependent Transcriptional Repressor Expression Vector A transcriptional repressor domain (KRAB) of a *Homo sapiens* zinc finger protein 10 Kox1 gene (X52332) was amplified and isolated by the PCR method (the obtained product is referred to as Gene 3). cDNA extracted and synthesized from HeLa cells was used as a template in the PCR. Primers used in the PCR were 5' primer oligo nucleotide: ggg gaa ttc aag ctt ggc ggt ggt gct ttg tct (SEQ ID NO: 11) and 3' primer oligo nucleotide: ggg gga tcc tta aac tga tga ttt gat ttc aaa tgc agt c (SEQ ID NO: 12).

Gene 3 was treated with restriction enzymes BamHI-HindIII, and it was then inserted into pBluescriptII containing a tetracycline-dependent receptor (TetR) that had been treated in the same manner as above, so as to produce TetR-KRAB (this is referred to as Vector 6). The plasmid vector, Vector 6, was treated with restriction enzymes BamHI-EcoRI, and it was then inserted into pBluescriptII containing PhCMV pro. that had been treated in the same manner as above, so as to produce PhCMV pro.-TetR-KRAB (this is referred to as Vector 7). The plasmid vector, Vector 7, was treated with restriction enzymes XhoI-BamHI, and it was then inserted into the plasmid vector, Vector 5, that had been treated in the same manner as above, so as to produce Vector 8.

(6) Ligation of Tetracycline-dependent Transcription Factors (PhCMV pro.-rTetR-VP16 and PhCMV pro.-TetR-KRAB (Kox1))

Both plasmid vectors Vector 4 and Vector 8 were treated with restriction enzymes XhoI-ApaI. A tetracycline-dependent transcriptional repressor expression gene was ligated to the tetracycline-dependent transcriptional activator expression plasmid vector, Vector 4, so as to produce Vector 9.

(7) Production of a (mev-1 Type) cyt-1 Gene (Referred to as Gene 4) into which an Electron Transport-Inhibiting (Active Oxygen-Excessively Producing) Mutant Gene is Inserted Using mice ICR liver cDNA (derived from mouse liver of an ICR line) as a template, a cytochrome b large subunit (cyt-1) was cloned by the PCR method. Primers used in the PCR were 5' primer oligo nucleotide: ggg gaa ttc gcc gcc acc atg gct gcg ttc ttg ctg aga cat gtc agc (SEQ ID NO: 13) and 3' primer oligo nucleotide: ggg aag ctt tct aga aaa tca cag ggc ggc cag ccc (SEQ ID NO: 14). An amplified DNA fragment of the cytochrome b large subunit obtained as above was introduced into the MCS (multi-cloning site)/restriction site EcoRI-XbaI of a pBluescript II SK– plasmid vector. Competent cells of *Escherichia coli* DH5α were produced, and the cells were then transduced with the above plasmid vector. Thereafter, a PCR amplified fragment of a gene of interest was isolated (subcloned).

In order to produce a (mev-1 type) cyt-1 gene into which an electron transport-inhibiting (active oxygen-excessively producing) mutant gene was inserted, the PCR and the subsequent genetic transduction were carried out in the same manner as described above, using 5' primer oligo nucleotide: ggg gaa ttc ctc ttc cca tgg cac tgt ccg aat gcc (SEQ ID NO: 15) and 3' primer oligo nucleotide: ggg aag ctt tct aga aaa tca cag ggc ggc cag ccc (SEQ ID NO: 16) as primers. Thereafter, subcloning of the 3' region of the mev-1 type cyt-1 gene was carried out.

The 3' region of the mev-1 type cyt-1 gene was inserted into the plasmid vector used in the subcloning of the full-length wild-type cyt-1 gene produced above, using restriction enzymes EarI-XbaI, so as to produce a full-length met-1 type cyt-1 gene.

(8) Production of Plasmid Vector Used for Expression of Gene of Interest (mev-1 type cyt-1 Gene) Using Tetracycline Gene Expression Control System (TRE)

A mev-1 type cyt-1 gene (Gene 4) was inserted into a pTRE plasmid vector (Clontech) treated with restriction enzymes EcoRI-XbaI, so as to produce Vector 10.

A pcDNA3 plasmid vector was treated with restriction enzymes NruI-EcoRI, so as to produce a pcDNA3 ACMV pro. plasmid vector from which a Cytomegalovirus promoter (CMV promoter) was eliminated (wherein the regenerated EcoRI site was also destroyed). (The obtained vector is referred to as Vector 11.) Vector 10 was treated with restriction enzymes XhoI-XbaI, so as to obtain a tetracycline receptor responsive element (TRE)-mev-1 cyt-1 gene. The obtained gene was inserted into Vector 11, which had been treated with restriction enzymes XhoI-XbaI in the same manner as above, so as to produce Vector 12.

(9) Insertion of Gene (Beta-Globin Insulator Sequence: Insulator) Acting to Insulate Cis-Element Effects Existing in Promoter and Transcriptional Control Region from Outside (Part 1)

An insulator DNA fragment was amplified and isolated by the PCR method (this is referred to as Gene 5). A chicken cDNA library was used as a template in the PCR. Primers used in the PCR were 5' primer oligo nucleotide: ggg gat atc ggg aca gcc ccc ccc caa ag (SEQ ID NO: 17) and 3' primer oligo nucleotide: ggg gat atc ctc act gac tcc gtc ctg g (SEQ ID NO: 18).

The amplified DNA fragment, Gene 5, was treated with a restriction enzyme EcoRV. Thereafter, it was inserted into a pBluescriptII SK-plasmid vector that had been treated with a restriction enzyme EcoRV in the same manner as above, so as to produce Vector 13. The plasmid vector, Vector 13, was treated with a restriction enzyme EcoRV, and the obtained insulator was then inserted into Vector 12, a plasmid vector treated with a restriction enzyme PvuII, so as to produce Vector 14.

(10) Production of Full-Length Tetracycline Gene Expression Control System Using Tetracycline Receptor Responsive Element (TRE)

Both Vector 9, a tetracycline-dependent transcription factor (activator and repressor) expression plasmid vector, and a plasmid vector used for the expression of a gene of interest (mev-1 type cyt-1 gene) using a tetracycline gene expression control system (TRE) were treated with restriction enzymes SspI-BglII. Thereafter, both plasmid vectors were ligated with each other, so as to produce Vector 15.

(11) Insertion of Gene (Insulator) Acting to Insulate cis-Element Effects Existing in Promoter and Transcriptional Control Region from Outside (Part 2)

Vector 13, an insulator-containing pBluescriptII SK-plasmid vector, was treated with a restriction enzyme EcoRV, and the obtained insulator was inserted into Vector 15, a plasmid vector treated with a restriction enzyme SspI, so as to produce Vector 16.

(12) Insertion of Gene (Insulator) Acting to Insulate cis-Element Effects Existing in Promoter and Transcriptional Control Region from Outside (Part 3)

Vector 13, an insulator-containing pBluescriptII SK-plasmid vector, was treated with a restriction enzyme EcoRV, and the obtained insulator was inserted into Vector 16, a plasmid vector treated with a restriction enzyme PmlI, so as to produce Vector 17.

(13) Insertion of Gene (Insulator) Acting to Insulate cis-Element Effects Existing in Promoter and Transcriptional Control Region from Outside (Part 4)

Vector 13, an insulator-containing pBluescriptII SK-plasmid vector, was treated with a restriction enzyme EcoRV, and the obtained insulator was inserted into Vector 17, a plasmid vector treated with a restriction enzyme EcoRV, so as to produce Vector 18, which was a tetracycline system full-length (integrated) plasmid vector. This Vector 18 was a transgene to produce an electron transport-inhibiting (active oxygen-excessively producing) mev-1 animal.

(14) Insertion of Reporter Protein (Nuclear-localized Green Fluorescent Protein: nlsGFP) Gene An nlsGFP DNA fragment was amplified and isolated by the PCR method (this is referred as Gene 6). A pEGFP-C1 plasmid vector containing GFP was used as a template in the PCR Primers used in the PCR were 5' primer oligo nucleotide: ggg tct aga aat att aag ctt tgc ggc cgc atg ccc aag aag aag cgc aag gtg gag gac gcc atg gtg agc aag ggc gag (SEQ ID NO: 19) and 3' primer oligo nucleotide: ggg ggt acc ggg ccc cgg atc cct tgt aca gct cgt cca tgc (SEQ ID NO: 20). The amplified and isolated nlsGFP gene, Gene 6, was treated with restriction enzymes ApaI-XbaI, and it was then inserted into Vector 18, a tetracycline system full-length (integrated) plasmid vector treated with the same above restriction enzymes, so as to produce Vector 19.

(15) Insertion of Reporter Protein (Luciferase) Gene

A luciferase DNA fragment was amplified and isolated by the PCR method (this is referred to as Gene 7). A luciferase-containing pCH110 or pMC1871 plasmid vector was used as a template in the PCR. Primers used in the PCR were 5' primer oligo nucleotide: ggg gga tcc atg gaa gac gcc aaa aac (SEQ ID NO: 21) and 3' primer oligo nucleotide: ggg ggt acc ggg ccc tta caa ttt gga ctt tcc gc (SEQ ID NO: 22). The amplified and isolated luciferase gene, Gene 7, was treated with restriction enzymes ApaI-BamHI, and it was then inserted into Vector 19, a tetracycline system full-length (integrated) plasmid vector treated with the same above restriction enzymes, so as to produce Vector 20.

(16) Insertion of Gene Sequence (IRES) Enabling Expression of Two Types of mRNA from One Type of Promoter An IRES-containing pBluescriptII SK-plasmid vector was treated with restriction enzymes HindIII-NotI, so as to obtain IRES. The IRES was inserted into Vector 20, a tetracycline system full-length (integrated) plasmid vector treated with restriction enzymes HindIII-NotI in the same manner as above, so as to produce Vector 21. This Vector 21 is s a transgene (tetracycline system transgene (insulator (+)): Tet system-Rep. Tg (+)), which is used to prove that the tetracycline system can strictly carry out inducible expression of a gene of interest by the effects of the insulator. In addition, a plasmid vector, which was a tetracycline system transgene (insulator (−): Tet system-Rep. Tg (−)), was obtained by omitting the steps described in (9) and (11) to (13).

(17) Production of Plasmid Vector Wherein Expression of Tetracycline-dependent Transcriptional Activator (rTetR-VP16) is Controlled by PhCMV Promoter A beta-globin gene intron 2, exon 3 region (beta-globin splice A/D) gene was amplified and isolated by the PCR method (this is referred to as Gene 8). A mouse cDNA library was used as a template in the PCR. Primers used in the PCR were 5' primer oligo nucleotide: ggg tct aga gcc tct gct aac cat gtt cat g (SEQ ID NO: 23) and 3' primer oligo nucleotide: ggg gaa tcc gaa ttc ttt gcc aaa atg atg aga cag cac (SEQ ID NO: 24). The amplified and isolated beta-globin splice A/D gene, Gene 8, was treated with restriction enzymes EcoRI-XbaI. It was also inserted into Vector 4, a tetracycline-dependent transcriptional activator expression plasmid vector treated with restriction enzymes EcoRI-NheI, so as to produce Vector 22.

(18) Production of Plasmid Vector Wherein Expression of Tetracycline-dependent Transcriptional Repressor (TetR-KRAB) is Controlled by PhCMV Enhancer-actin Promoter A beta-actin promoter region (beta-actin pro.) gene was amplified and isolated by the PCR method (this is referred to as Gene 9). A mouse cDNA library was used as a template in the PCR. Primers used in the PCR were 5' primer oligo nucleotide: ggg gga tcc tac gta tcg agg tga gcc cca cgt tc (SEQ ID NO: 25) and 3' primer oligo nucleotide: ggg gaa ttc tct aga gcc gcc ggt cac gcc aga ag (SEQ ID NO: 26). The amplified and isolated beta-actin pro. gene, Gene 9, was treated with restriction enzymes SnaBI-XbaI, and it was then inserted into a pcDNA3 plasmid vector treated with the same restriction enzymes, so as to produce Vector 23.

The beta-actin pro. was ligated to a CMV enhancer (CMV enhancer-beta-globin pro.). This is to say, Vector 23, which was a pcDNA3 plasmid vector, and Gene 8, which was a beta-globin gene intron 2, exon 3 region (beta-globin splice A/D) gene fragment, were treated with restriction enzymes EcoRI-XbaI. Thereafter, the beta-globin splice A/D was inserted into Vector 23, so as to produce Vector 24.

Vector 8, a tetracycline-dependent transcriptional repressor plasmid vector, was treated with restriction enzymes NruI-KpnI, so that the CMV pro. of a pcDNA 3 plasmid vector existing in Vector 8 was eliminated (this is referred to as Vector 25). Vector 24, which was a (CMV enhancer-beta-globin pro.-beta-globin splice A/D) pcDNA3 plasmid vector obtained by ligating the beta-globin splice A/D to CMV enhancer-beta-globin pro., was treated with restriction enzymes EcoRI-SpeI. Thereafter, the CMV enhancer-beta-globin pro.-beta-globin splice A/D was inserted into the aforementioned Vector 25, which had been treated with the same restriction enzymes (this is referred to as Vector 26).

(19) Production of Tetracycline System Full-length (Integrated) Plasmid Vector for Strictly Controlling Inducible Gene Expression with Tetracycline-like Agent Vector 22, which was a plasmid vector wherein the expression of a tetracycline-dependent transcriptional activator (rTetR-VP16) was controlled by a PhCMV promoter, and Vector 26, which was a plasmid vector wherein the expression of a tetracycline-dependent transcriptional repressor (TetR-KRAB) was controlled by a PhCMV enhancer-actin promoter, were treated with restriction enzymes ApaI-XhoI. Thereafter, Vector 26 was ligated to Vector 22, so as to produce Vector 27.

A blunt-ended insulator (treated with a restriction enzyme EcoRV) was inserted into the PmlI restriction site of the above plasmid vector, Vector 27, so as to produce Vector 28. The above plasmid vector, Vector 28, was treated with restriction enzymes NheI-NruI, and it was then inserted into Vector 21, a tetracycline system full-length (integratied) plasmid vector treated with the same above restriction enzymes, so as to produce Vector 29. That is, Vector 29 is the transgene of the present invention (tetracycline system transgene: Tet system-Rep Tg AD (+)), which enables the strict control of inducible expression of a tetracycline gene due to competition of transcriptional regulators at 2 stages (a binding competition of a transcription factor to a CMV enhancer, and a binding competition of a tetracycline-dependent transcriptional regulator to TRE).

A mev-1 type cyt-1 gene was introduced into the tetracycline system transgene, so as to produce Tet system-mev-1 Tg AD (+). The structure is shown in FIG. 7.

(B) Production of mev-1 Conditional Transgenic Mouse

A small amount of the Tet system-mev-1 Tg AD (+) produced in (A) above was injected into the male pronucleus of the pronucleus-stage fertilized egg of a mouse. Injection of such small amount of the Tet system-mev-1 Tg AD (+) was carried out according to common methods regarding microinjection.

(C) Screening for mev-1 Conditional Transgenic Mouse

Genomic DNA was extracted from the tail of a baby mouse obtained by the method described in (B) above. Thereafter, a mev-1 type cyt-1 gene contained in the transgene was amplified by the PCR method. mev-1 conditional transgenic mice of interest were screened depending on whether or not the mev-1 type cyt-1 gene was amplified (the results are shown in FIG. 8), so as to obtain a mev-1 conditional transgenic mouse of interest.

INDUSTRIAL APPLICABILITY

Using the transgenic animal cell and the transgenic non-human mammal of the present invention, it became possible to examine the action of reactive oxygen species (ROS) derived from mitochondria in mammals. In addition, the transgenic animal cell and the transgenic non-human mammal of the present invention are also useful for screening for a substance having action to suppress reactive oxygen species (ROS).

The invention claimed is:

1. An isolated recombinant animal cell comprising a mutant SDHC gene derived from a mouse, wherein the mutant SDHC gene encodes a protein having the amino acid sequence of SEQ ID NO: 1, wherein said mutant SDHC gene is expressed and wherein said isolated recombinant animal cell is characterized by a production of reactive oxygen species (ROS) at a greater level than in an isolated animal cell that does not express the mutant SDHC gene.

2. The animal cell according to claim 1, wherein apoptosis is induced at a greater rate than in the isolated animal cell that does not express the mutant SDHC gene.

3. The animal cell according to claim 1, which has a higher susceptibility to tumorigenesis than the isolated animal cell that does not express the mutant SDHC gene.

4. A recombinant vector for the production of the isolated recombinant animal cell according to claim 1 comprising a gene encoding the protein of SEQ ID NO: 1.

5. A method of screening for a substance having an action to suppress excessive reactive oxygen species (ROS), comprising:

providing the isolated recombinant animal cell of claim 1; and testing the activity of said substance to suppress reactive oxygen species (ROS) in said isolated recombinant animal cell.

6. The screening method according to claim 5, wherein the substance having an action to suppress excessive reactive oxygen species (ROS) is an apoptosis inhibitor or anticancer agent.

* * * * *